US008903192B2

(12) United States Patent
Malik et al.

(10) Patent No.: US 8,903,192 B2
(45) Date of Patent: Dec. 2, 2014

(54) NOISE REDUCTION OF IMAGING DATA

(75) Inventors: Wasim Q. Malik, Cambridge, MA (US); James Matthew Schummers, Palm Beach Gardens, FL (US); Mriganka Sur, Cambridge, MA (US); Emery Neal Brown, Brookline, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 144 days.

(21) Appl. No.: 12/904,627

(22) Filed: Oct. 14, 2010

(65) Prior Publication Data
US 2012/0093376 A1 Apr. 19, 2012

(51) Int. Cl.
G06K 9/40 (2006.01)
G06K 9/00 (2006.01)

(52) U.S. Cl.
CPC ............ G06K 9/0014 (2013.01); G06K 9/0051 (2013.01)
USPC .......................................... 382/275; 382/128

(58) Field of Classification Search
None
See application file for complete search history.

(56) References Cited

U.S. PATENT DOCUMENTS

| | | | |
|---|---|---|---|
| 5,616,504 A | 4/1997 | Brown et al. | |
| 5,792,051 A | 8/1998 | Chance | |
| 7,085,426 B2 | 8/2006 | August | |
| 7,372,985 B2 | 5/2008 | So et al. | |
| 7,557,929 B2 | 7/2009 | Fang-Yen et al. | |
| 7,711,416 B1 | 5/2010 | Akkin et al. | |
| 2002/0028010 A1* | 3/2002 | Toida ............................ | 382/131 |
| 2002/0186874 A1 | 12/2002 | Price et al. | |
| 2003/0118246 A1* | 6/2003 | August ........................ | 382/260 |
| 2004/0115126 A1* | 6/2004 | Ross et al. ..................... | 424/1.41 |
| 2004/0254474 A1* | 12/2004 | Seibel et al. ................... | 600/473 |
| 2005/0123181 A1* | 6/2005 | Freund et al. ................. | 382/128 |
| 2006/0241788 A1 | 10/2006 | Srinivasan et al. | |
| 2006/0282008 A1* | 12/2006 | Hu et al. ......................... | 600/558 |
| 2008/0138289 A1* | 6/2008 | Goronkin et al. .............. | 424/9.4 |
| 2008/0171906 A1* | 7/2008 | Everaerts et al. ............... | 600/36 |
| 2008/0260232 A1* | 10/2008 | Ohara et al. .................... | 382/132 |
| 2008/0310751 A1* | 12/2008 | Rai et al. ........................ | 382/264 |
| 2009/0076380 A1* | 3/2009 | Thierman ..................... | 600/425 |
| 2009/0143685 A1* | 6/2009 | Elner et al. .................... | 600/476 |
| 2009/0153132 A1 | 6/2009 | Tufillaro et al. | |

(Continued)

FOREIGN PATENT DOCUMENTS

WO WO 2006/127967 11/2006

OTHER PUBLICATIONS

Malik et al.—Renaud, Sylvie, ed. Neurocomp'09 Computational Neuroscience: From Multiple levels to Multi-level, Sep. 16-18, 2009, Bordeaux, France.*

(Continued)

Primary Examiner — Nirav G Patel
(74) Attorney, Agent, or Firm — McCarter & English, LLP

(57) ABSTRACT

The present invention relates to systems and methods for reducing noise in image data. Preferred embodiments relate to methods for analyzing two-photon in vivo imaging of biological systems. With neuronal population imaging with subcellular resolution, this modality offers an approach for gaining a fundamental understanding of brain anatomy and physiology. Analysis of calcium imaging data requires denoising, that is separating the signal from complex physiological noise. To analyze two-photon brain imaging data, for example, harmonic regression plus colored noise model and an efficient cyclic descent algorithm for parameter estimation. This approach reliably separates stimulus-evoked fluorescence response from background activity and noise, assesses goodness of fit, and estimates confidence intervals and signal-to-noise ratio.

48 Claims, 14 Drawing Sheets

(56) References Cited

U.S. PATENT DOCUMENTS

| | | | | |
|---|---|---|---|---|
| 2009/0161980 | A1* | 6/2009 | Wang et al. | 382/264 |
| 2009/0214113 | A1* | 8/2009 | Oztan et al. | 382/167 |
| 2009/0326379 | A1* | 12/2009 | Daigle et al. | 600/453 |
| 2010/0033180 | A1 | 2/2010 | Biber et al. | |
| 2010/0160250 | A1* | 6/2010 | Douglass et al. | 514/46 |
| 2010/0168532 | A1 | 7/2010 | Waziri et al. | |
| 2010/0190229 | A1 | 7/2010 | Zhang et al. | |
| 2010/0249609 | A1 | 9/2010 | Akkin et al. | |
| 2010/0278399 | A1* | 11/2010 | Bednarkiewicz et al. | 382/128 |
| 2011/0046504 | A1* | 2/2011 | Pradeep et al. | 600/544 |
| 2011/0170180 | A1* | 7/2011 | Turner et al. | 359/385 |

OTHER PUBLICATIONS

Malik et al., "A Statistical Model for Multiphoton Calcium Imaging of the Brain," 31$^{st}$ Annual International Conference of the IEEE EMBS, Minneapolis, Minnesota, USA, Sep. 2-6, 2009.

Sornborger et al., "Spatiotemporal Analysis of Optical Imaging Data," Academic Press, Science Direct, www.sciencedirect.com, 2003 Elsevier Science.

Greenberg et al., "Population Imaging of Ongoing Neuronal Activity in the Visual Cortex of Awake Rats," Nature Neuroscience, vol. 11, No. 7, Jul. 8.

Gabbay et al., "A Principal Components-Based Method for the Detection of Neuronal Activity Maps: Application to Optical Imaging," Neuroimage 11, 313-325 (2000).

Schummers et al., "Tuned responses of astrocytes and their influence on hemodynamic signals in the visual cortex," Science, vol. 320, Jun. 20, 2008, www.sciencemag.org.

Mrsic-Flogel et al., "Brain mapping: new wave optical imaging," Current Biology, vol. 13, R778-R780, Sep. 30, 2003.

Purdon et al., "Locally regularized spatiotemporal modeling and model comparison for functional MRI," NeuroImage 14, 912-923 (2001).

Brown et al., "A statistical model of the human core-temperature circadian rhythm," Am. J. Physical Endocrinol Metab 279: E669-E683, 2000.

Majewska et al., "A custom-made two-photon microscope and deconvolution system," Pfluger Arch—Eur J Physiol (2000) 441:398-408.

Kalatsky et al., "New paradigm for optical imaging: temporally encoded maps of intrinsic signal," Neuron, vol. 38, 529-545, May 22, 2003.

Kerr et al., "Imaging in vivo, Watching the Brain in Action," Nature Reviews, Neuroscience, vol. 9, Nature Publishing Group, Mar. 2008.

Lillis et al., "Two-photon imaging of spatially extended neuronal network dynamics with high temporal resolution," Journal of Neuroscience Methods, 172 (2008) 178-184.

Brown et al., "A statistical model of the human core-temperature circadian rhythm," Am J Physical Endocrinol Metab., 279: E669-E683, 2000.

Mukamel et al., "Automated analysis of cellular signals from large-scale calcium imaging data," Neuron 63, 747-760, Sep. 24, 2009.

* cited by examiner

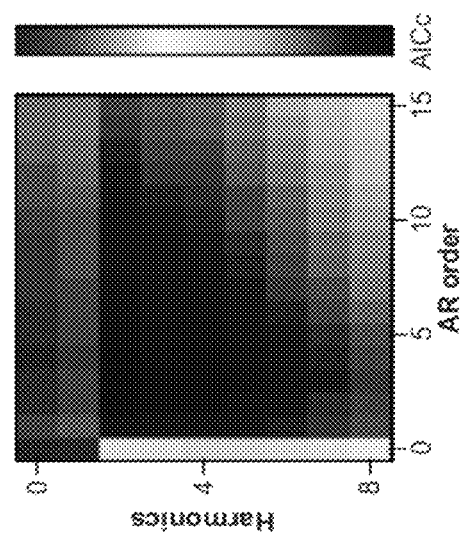
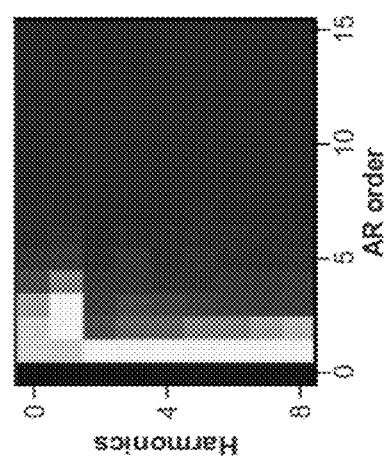
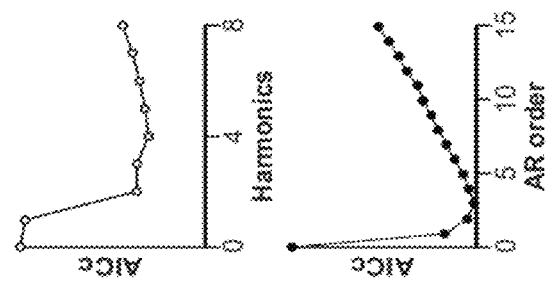
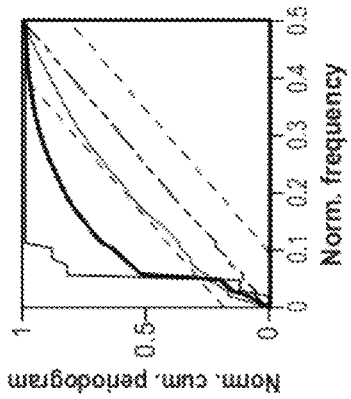
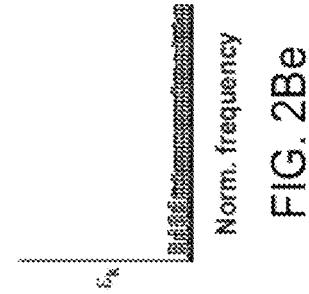
FIG. 2Ba  FIG. 2Bb  FIG. 2Bc  FIG. 2Bd  FIG. 2Be

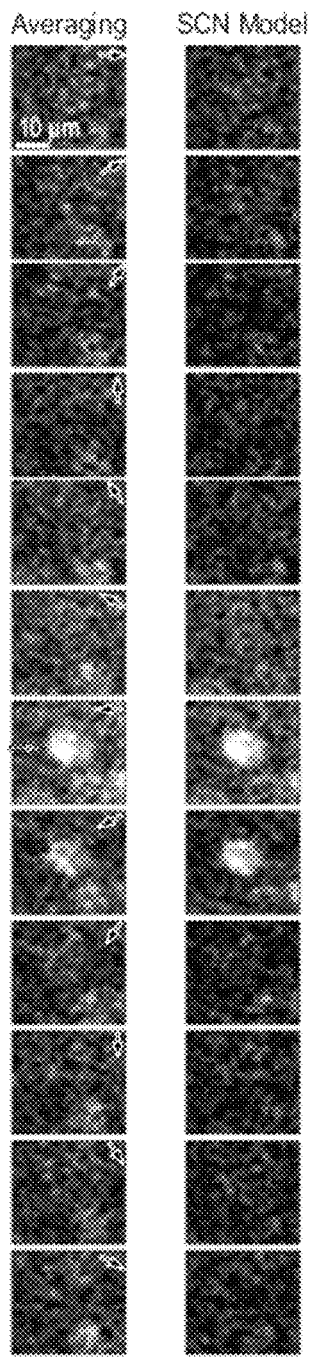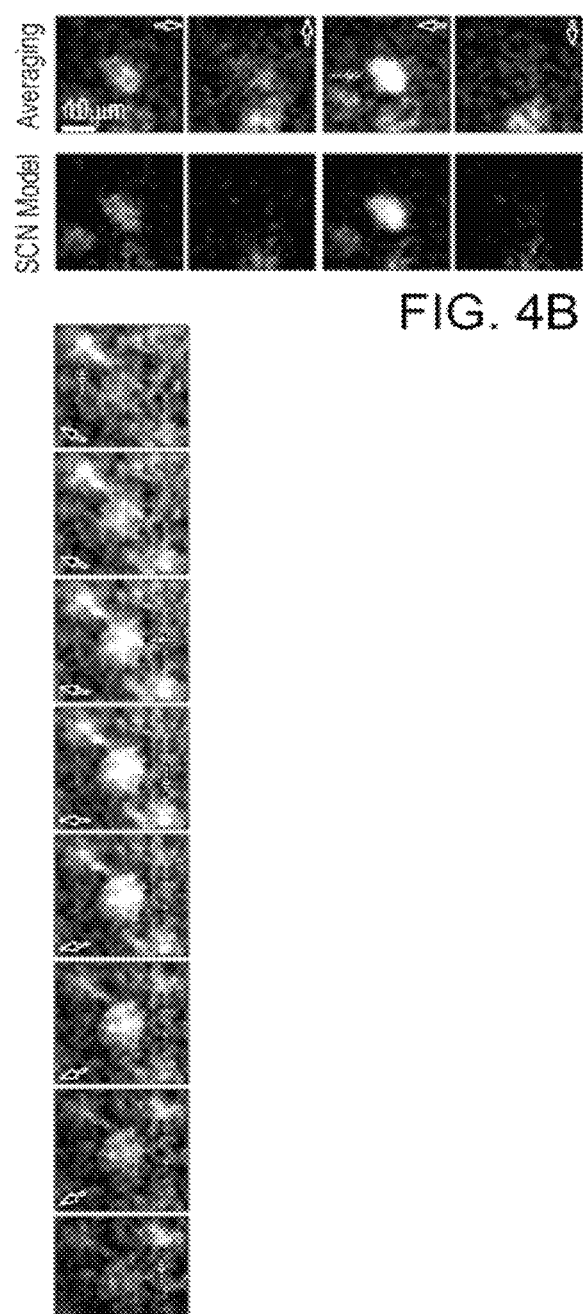
FIG. 4B
FIG. 4A  FIG. 4C

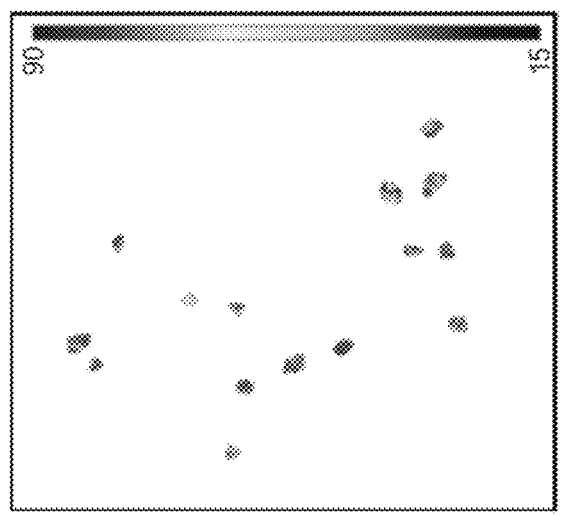
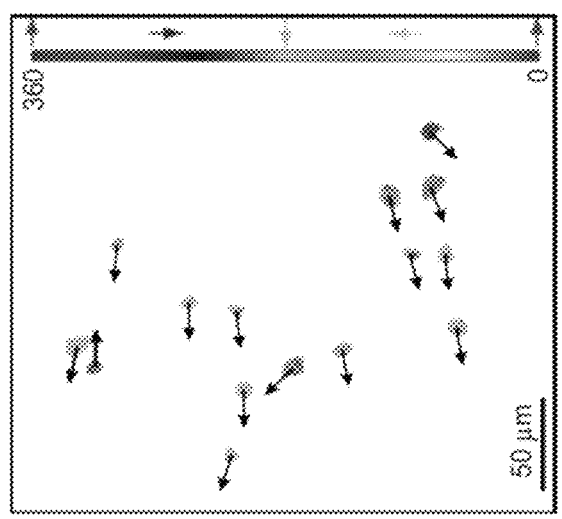
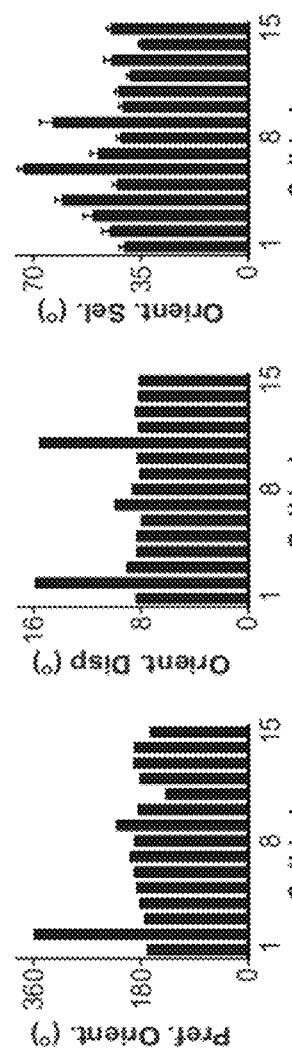

NOISE REDUCTION OF IMAGING DATA

BACKGROUND OF THE INVENTION

Various imaging modalities have been developed to measure biological systems. Two-photon microscopy, for example, is now recognized as a valuable tool for real-time in vivo imaging of biological systems. A two-photon microscope excites fluorophores in a volume of biological sample using pulsed lasers to induce the emission of a fluorescence signal. Typically, a focused laser beam scans the tissue in a two-dimensional raster pattern, producing a fluorescence image that typically spans hundreds of cells. The images facilitate highly informative and quantitative analyses with a range of biological applications.

Properly separating signal from noise, often termed denoising, is a crucial signal processing procedure in the analysis of imaging data. While there has been considerable success in the development of imaging systems, such as two-photon microscopy, the corresponding signal processing methodology has received less attention. The observed fluorescence response depends upon several factors: 1) the nature of the stimulus and the modulation of neural activity due to the stimulus; 2) movements due to highly structured physiological processes; 3) spontaneous neural activity; and 4) optical and electrical noise. Existing methods for processing two-photon data consist of averaging the measured fluorescence levels over multiple trials followed by kernel-based smoothing or fitting an appropriate curve to these time-series data. Averaging, while highly intuitive and easy to perform, requires a large number of trials which is often not possible in two-photon imaging measurements.

Thus, there is a continuing need for improvements in the processing of image data to improve the speed and usefulness of such systems and methods.

SUMMARY OF THE INVENTION

The present invention relates to systems and methods for the processing of collected data of dynamic processes. Preferred embodiments record the response to a stimulus, and process the measured response to remove noise from the measured data. The dynamic process and the noise embedded in the collected data are represented by analytic expressions that are selected to reduce computational complexity using an iterative process that converges to a solution for each expression. Thus, for embodiments using a selected form of stimulus and a system used for measuring the physiologic response to the stimulus, statistical methods are employed to separate signal and noise, assess goodness of fit and determine characteristics of physiological features in the image. A preferred embodiment uses a statistical signal plus correlated noise (SCN) model for the analysis of imaging data.

In a preferred embodiment, a periodic stimulus induced structure is represented as a harmonic regression and the temporally correlated noise is represented as an autoregressive process. Preferred embodiments utilize a computationally efficient cyclic descent algorithm for maximum likelihood estimation of the model parameters. The low computational cost requirements of the algorithm makes it amenable to automated analysis of large imaging data sets. By analyzing two-photon calcium imaging data, for example, that has been recorded from the ferret primary visual cortex, this method has demonstrated the accurate modeling of the recorded data and provides substantial reduction of the noise present in the images.

Two-photon calcium imaging is an important tool for visualizing function in biological systems in real time and near real-time measurements. In the brain, two-photon calcium imaging makes it possible to view population neuronal activity and to resolve features at the subcellular level. While much progress is rapidly being made on devising faster and higher resolution imaging instruments, the development of statistical analysis methods to accurately and efficiently extract the desired two-photon signal from the complex highly structured noise processes has received less attention. The present invention can utilize methods such as a Volterra series representation to formulate a solution in which a nonlinear process is separated into a plurality of linear representations. This can include a first linear representation of a dynamic process such as the physiologic response to the stimulus and a second linear representation of the noise contained in the measured data.

Preferred embodiments of the present invention use statistical methods that are based on a harmonic regression plus correlated noise model for rapidly and efficiently analyzing two-photon imaging data. The orders of the harmonic and autoregressive components can be determined by an automated procedure and used to reduce computational complexity. This flexible model provides a parsimonious representation in which the signal, stimulus evoked fluorescence response, is separated from the background activity and noise. Assessments of model confidence intervals and signal-to-noise ratios are provided. A preferred embodiment includes an analysis of calcium fluorescence imaging data recorded in vivo from the ferret visual cortex at cellular resolution. The method is computationally efficient and can be used with other models for imaging data and to implementations for real-time measurement and high-throughput imaging analyses.

Two-photon imaging of calcium-sensitive fluorescent indicators to investigate neural physiology is particularly appealing because the measured fluorescence is closely related to neural activity. This imaging modality enables analysis of a broad spatial scale, ranging from the structure of dendritic spines (microns) to the architecture of neuronal networks (millimeters), as well as analysis of a broad temporal scale from fast action potentials (milliseconds) to slow calcium waves (seconds).

Preferred embodiments of the invention utilize a computer implemented analysis to solve this signal plus colored noise problem. Colored noise appears in many contexts in computational biology, including functional magnetic resonance imaging, neural voltage-sensitive dye imaging, circadian rhythms, synaptic background activity in cortical neurons, gene regulatory networks, speech signals, cell locomotion patterns, and many others. Colored noise is also encountered in astronomy, analog electronics, wideband communications, and many other areas. The procedures usually applied to these problems, based on expectation maximization or exact maximum-likelihood procedures, are often computationally intensive. The present invention utilizes an alternate approximate maximum likelihood procedure that can be applied to a range of such problems, thereby providing advantages for real-time computation and high-throughput processing.

Additional embodiments can employ additional forms of stimulus, such as auditory or electrical signals or mechanical or electromechanical devices to contact an organism or mammalian body. The response to the sensory stimulus can also be measured by other imaging systems, such as magnetic resonance imaging (fMRI) or diffuse optical tomography (DOT). Besides the measurement of response to a stimulus, other possible embodiments can involve analyzing system dynamics without the application of a stimulus.

BRIEF DESCRIPTION OF THE DRAWINGS

FIG. 1Ba shows an anatomical image of cell population at 150 µm depth obtained by plotting the pixel-wise maximum fluorescence across the movie frames obtained under a rotating orientation stimulus; The ROIs indicate two neighbouring neurons identified manually, Cell 11 (blue) and Cell 12 (red); Brighter shades represent higher fluorescence intensity; FIG. 1Bb show relative fluorescence time-traces for each of the two neurons highlighted in FIG. 1Ba under three trials of stimulus application with orientation indicated by arrows; The solid line and background region show the mean±std computed across all of the pixels comprising the given cell; Vertical dashed lines mark trial boundaries, at which the stimulus is oriented at 0° with respect to the positive x-axis (horizontal); The structure rotates counter-clockwise from there; The response of Cell 12, unlike Cell 11, is specific to the direction of orthogonal drift; It exhibits an excitatory response at horizontal orientation for one drift direction (180° orientation) but not the other (0° orientation).

FIG. 1Ca is an anatomical image of a population of 15 cells; Brighter gray shades represent higher fluorescence intensity, and ROIs and cell indices indicate all of the cells identified manually; FIG. 1Cb shows the orientation tuning curve of each cell obtained by averaging the measured relative fluorescence across three trials;

FIG. 2Aa shows iterative estimates of the model parameters, namely the residual variance ($\sigma^2$), intercept ($\mu$), harmonic coefficients ($a_i$ and $b_i$; i=1, ..., h) and autoregressive coefficients ($a_j$; j=1, ..., p), for the fluorescence time series in FIG. 3Ba; FIG. 2Ab shows the percentage difference between the successive estimates of the model parameters in FIG. 2Aa. For the $l^{th}$ iteration, the quantity shown is calculated as $\Delta\mu^{(l)}=|(\mu^{(l)}-\mu^{(l-1)})/\mu^{(l)}|\times 100$, where $\mu^{(l)}$ is the estimate of parameter $\mu$ at the $i^{th}$ iteration and $\mu^{(0)}=0$. The y-axis has a logarithmic scale.

FIGS. 2Ba-2Be show model order selection and goodness of fit for fluorescence time series data from Cell 11; In FIG. 2Ba shows corrected Akaike information criterion (AICc) as a function of the harmonic (h) and autoregressive model orders (p); The minimum of this surface is achieved with h=2 and p=2; The quantity shown is the AICc normalized to that obtained with h=p=0; In the pseudo-color heat map, red and blue represent large and small AICc values, respectively; In FIG. 2Bb Left: AICc as a function of the harmonic order when a signal-only model is assumed and the AR component is not included; The optimal harmonic order, as indicated by the minimum AICc, is h=4; Right: AICc as a function of the AR order when a signal-plus-colored-noise model is assumed with h=4; The optimal AR order, as indicated by the minimum AICc, is p=2; FIG. 2Bc shows the percentage of image pixels of the cell whose time series data estimate with the model yields substantially white residuals as determined by the Ljung-Box test. Various combinations of the harmonic and AR model orders are shown; Noticeably, the model order determined to be optimal by AICc is not sufficient for achieving whiteness, and a higher-order AR fit is needed; For h=4, the whiteness criterion is satisfied for all of the pixels by an AR order of at least 8; In the pseudo-color heat map, blue and red represent 0 and 100%, respectively; In FIG. 2Bb the spectra obtained using the FFT, illustrating the decomposition of the fluorescence time series data $f_k$ (black) into $\hat{s}_k$, the estimated stimulus-evoked signal component and baseline fluorescence (blue), $\hat{v}_k$, stimulus-free background activity (red), $\hat{\epsilon}_k$, and the residual white noise (green); The dominant lower-frequency components visible in the data correspond to the response to the stimulus and are captured by $\hat{s}_k$ which has a line spectrum at 4 harmonics of the stimulus frequency; The rest of the measured activity, with a non-uniform spectrum, is captured by the AR component; The spectrum of the AR residual is substantially uniform, confirming whiteness; In FIG. 2Be the normalized cumulative periodograms (NCPs) of the four components in FIG. 2Bd, along with the 95% bounds for whiteness (dashed lines) and the NCP of ideal white noise (dotted line); The presence of temporal correlation in the background activity, $\hat{v}_k$, is evident from this plot (red line), while the residuals lie well within the bounds for independence;

In FIG. 3Aa the AICc surface for each of the cells in the data-set averaged across the pixels for that cell (blue: low; red: high); FIG. 3Ab shows AICc as a function of the harmonic order when an AR component is not fit to the residual of the harmonic regression; FIG. 3Ac shows AICc as a function of the AR order when the optimal harmonic order from b is used; FIG. 3Ad shows percentage of pixels of each cell that pass the Ljung-Box whiteness test (blue: 0%; red: 100%);

FIG. 3Ba shows relative fluorescence data $f_k$ (blue) measured in three consecutive trials (boundaries marked by dashed lines) and the estimate $\hat{f}_k$ obtained by the signal plus colored noise model (red); FIG. 3Bb shows relative fluorescence data $f_k$ (blue) and the estimate of its signal component $\hat{s}_k$ showing the denoised stimulus-evoked activity (red); FIG. 3Bc shows the autocorrelation function (red) of the model residuals, $\hat{\epsilon}_k$, lies within the 95% bounds for whiteness (blue); The autocorrelation values are used to compute the Ljung-Box (LB) test statistic, from which goodness-of-fit determined is as shown in FIG. 2Bc; FIG. 3Bd shows the quantile-quantile plot of the residuals confirms Gaussianity; The results in FIG. 3Bc and 3Bd prove that the residuals are independently and identically distributed Gaussian, and all of the systematic variance in the data has been explained by the harmonic regression and autoregressive terms; FIG. 3Be shows the orientation tuning curve obtained from the denoised signal estimate in FIG. 3Bb; The model provides a smooth fit to the across-trials mean of the data; The point-wise approximate 95% confidence intervals are also shown. This model preserves the complex shape of the response tuning curve, which would be lost in conventional schemes that fit a symmetric cosine or Gaussian curve to neuronal response data.

FIGS. 4A-4C show image denoising and visualization of calcium activity; In FIG. 4Aa Fluorescence ($\Delta f_k$) response images from the area around a representative cell (Cell 14, soma marked by blue arrow) to orientation stimulus processed with conventional across-trial averaging and with this SCN model; Successive frames show the response at orientations, indicated by pink arrows, in 30° steps; The stimulus-free activity is removed by the SCN model; In FIG. 4Ba Fluorescence response of Cell 1 along four orientations, with the soma indicated by blue arrow; and in FIG. 4C shows the fluorescence response of Cell 12 obtained from the SCN model in 10° steps of orientations with successive frames acquired at 1 Hz; Slow calcium waves flowing across the cell processes (green arrow) and soma (blue arrow) can be observed due to the enhanced clarity and contrast of the denoised image.

FIG. 5A-5E illustrate the spatial distribution of preferred orientation and orientation selectivity after denoising with the signal plus colored noise (SCN) model; FIG. 5A shows a spatial map of visual response characteristics for pixels that lie within cell boundaries identified manually from FIG. 1Ba; a pixel-wise preferred orientation is indicated by the colormap, and the mean preferred orientation of the cell is indicated by the black arrow originating from the centre of each cell. Colorbar and colored arrows represent the orientation scale in degrees; FIG. 5B shows orientation selectivity, a measure of tuning sharpness evaluated as the half-width range at half-height response, is indicated by the colormap; The colorbar represents the orientation selectivity in degrees; FIG. 5C shows cell-wise preferred orientation according to cell indices defined in FIG. 1Aa, evaluated as the mean of the preferred orientation across all of the pixels in a cell (errorbars indicate 95% confidence intervals on the mean); FIG. 5D shows circular dispersion of the cellular orientation response; and FIG. 5E shows orientation selectivity of the cell (mean±sem across pixels).

FIG. 6A shows the signal power ($P_s$), noise power ($P_v$), and SNR of all 15 neurons (mean±sem computed across pixels); and FIG. 6B shows a spatial map of SNR at each pixel in dB which agrees closely with the anatomical map in FIG. 1Ba.

DETAILED DESCRIPTION OF THE INVENTION

Figure 1A:
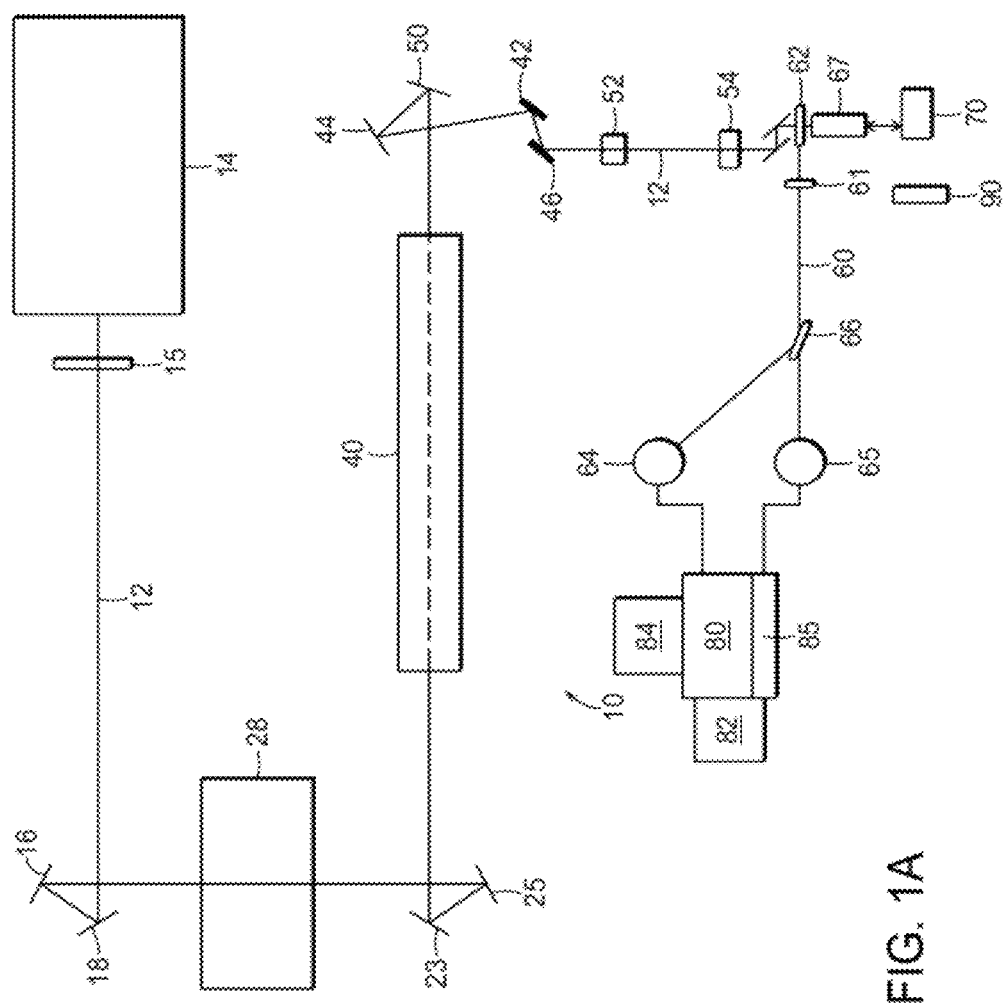
FIG. 1A shows two-photon fluorescence imaging system used in a preferred embodiment of the invention.

The present invention relates to systems and methods for processing data measuring the dynamics of systems. Preferred embodiments include systems and methods for measuring the response of biological systems to a stimulus. The measurement of such stimulus typically contains the physiologic response and physiological noise as well as noise from the measurement system.

Preferred embodiments of the present invention relate to a flexible local likelihood framework for analyzing imaging data. Preferred systems and methods appreciably enhance image contrast on a pixel-by-pixel basis by using an a signal plus colored noise (SCN) model to separate the salient stimulus-evoked neural responses in two-photon imaging data from the complex forms of physiological and recording noise common to such two-photon imaging measurements. A cyclic descent algorithm provides a computationally efficient approach for fitting the SCN model to the time-series of fluorescence responses. This process provides significantly denoised images (i.e. at each pixel, or selected groups of pixels, of the image) of neuronal populations, for example (FIGS. 5A-5E), and for tracking with improved subcellular resolution the temporal dynamics of individual neurons (FIGS. 4A-4C).

First, this analysis framework has been applied, for example, to analyze neuronal response to a continuous and periodic stimulus, such as to visual cortex cells. However, it can be extended to other two-photon imaging protocols using other stimuli. For example, in two-photon imaging measurements the stimulus is applied either in a random noise-like manner to avoid anticipatory responses, or by interspersing blank frames with no relevant excitatory or inhibitory stimulus present. With some types of stimuli, the neural response can undergo a sharp transition at a specific stimulus threshold. Repeated trials with such a stimulus yield responses that resemble more a series of square waves than a sinusoid. Such a square wave pattern can be represented more efficiently by using Walsh functions as a basis set in lieu of sines and cosines. To apply this approach to data recorded from any of these measurements, simply replace the stimulus represented as a harmonic regression in the current SCN model with an appropriate formulation of the stimulus model for the given protocol. The remainder of the analysis paradigm, including model fitting, model selection, goodness-of-fit assessment and inference, then proceeds as described herein.

Second, a signal plus Gaussian noise model is used in the analysis. However, in two-photon microscopy and other optical imaging modalities, the measured fluorescence intensity is a function of the discrete number of incident photons, and is therefore fundamentally a counting process and not necessarily Gaussian. The counting process nature of the two-photon measurements becomes more apparent as the acquisition rate increases. Furthermore, the measured fluorescence in some two-photon imaging measurements may also exhibit non-Gaussian behaviour due to distortions introduced during acquisition or post-processing. If the Gaussian model is not effective for a particular application, an alternative likelihood approach based on appropriately chosen non-Gaussian models can be used. For example, the neuronal spike trains can be extracted from two-photon data using template deconvolution. In this case, non-Gaussian likelihoods based on the theory of point processes and implemented using the generalized linear model can be adapted to analyze these two-photon imaging data.

Third, the time-series of neural responses in each pixel can be modelled separately, and does not consider inter-pixel dependencies. Dependencies among the pixels are present because: the activity of a single cell is captured across multiple pixels; retinotopy and network dependencies may lead to similar behaviour in contiguous regions of the image; and data pre-processing procedures, such as spatial smoothing, introduce correlations. This problem currently confronts all biological imaging modalities and can be addressed by formulating appropriate biologically-based spatio-temporal models. However, due to its low computational complexity, the present analysis can be readily adapted to conduct large-volume, high-throughput imaging data analyses in real-time, even including adjusting for interpixel coupling.

Imaging was performed with a two-photon laser scanning microscope 10 shown in FIG. 1A which uses a broadband laser light source 14 which can generate approximately 100 fsec pulses at 80 MHz. Using a shutter 15 and mirrors 16, 18 to direct illuminating light 12 from laser 14 through a Pockels cell or acoustic optic deflector 28. Beam path optics 40, including an alignment cage, focusing optics and a pinhole, directs the illuminating light to mirrors 44, 50 and onto first and second scanners 42, 46. The scanners deflect an beam using a pair of moving mirrors (galvanometers or AODs) that optically couple the illuminating beam 12 into the microscope assembly with a beam expanding lens 52 and a collimating lens 54. The beam incident on the tissue to be scanned is directed through a objective lens 67. The response beam 60 from the sample 70, such as brain tissue, is deflected by beamsplitter 62 through short pass filter 61 and measured by photomultiplier tubes 64, 65 with the returning light 60 separated into first and second components by a beamsplitter 66. The detected data is delivered to image processor 80 for processing, storage in electronic or optical memory 82 and display 84. Fluorescence was detected using photomultiplier tubes in whole-field detection mode and a 20×, 0.95 NA lens. The layer 2/3 area used for imaging was readily distinguished from layer 1 on the basis of the relative density of astrocytes and neurons. Visual stimuli were delivered via a 17" LCD display 90 placed 0.15 m away from the eyes an the animal 70. Thus, the system measures a response using the visual cortex of a mammalian subject, for example. The stimuli were generated with Matlab using the PsychoPhysics Toolbox. Neurons with relative fluorescence clearly distinguishable from the neuropil were chosen for subsequent cellular analysis. The output of the detector system is transmitted to a data processing system or computer 80. The image data can be stored in the storage device 82 and displayed on display 84. The data processor 85 or filter can be implemented using an application specific integrated circuit (ASIC). The image data can be accessed externally using a dedicated communication network or a public access network. The system 80 can also be programmed using software to perform the computer implemented operations described herein and/or to control a stimulation source 90, such as a display of other source as described herein.

Figure 1B:
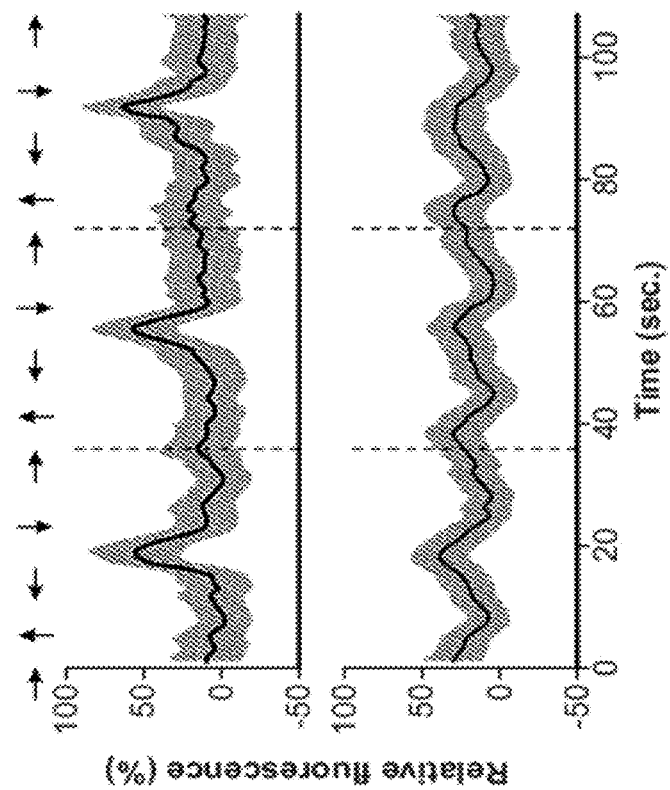
FIGS. 1Ba-1Bb show an example of two-photon fluorescence image and individual cell dynamics.
Figure 1B:
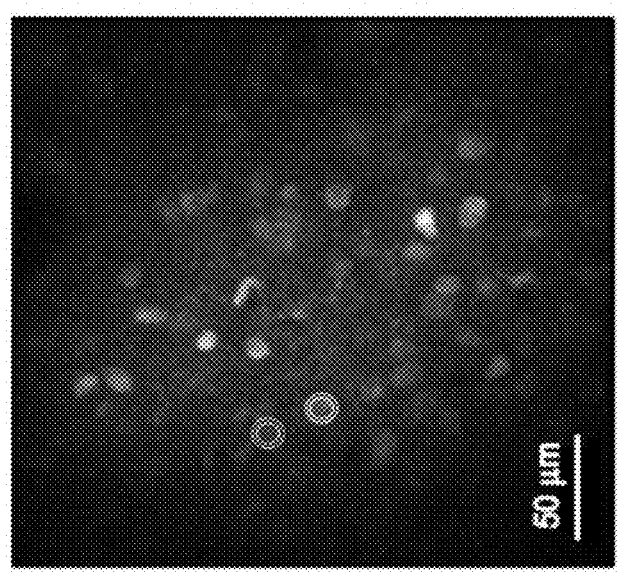
Figure 1C:
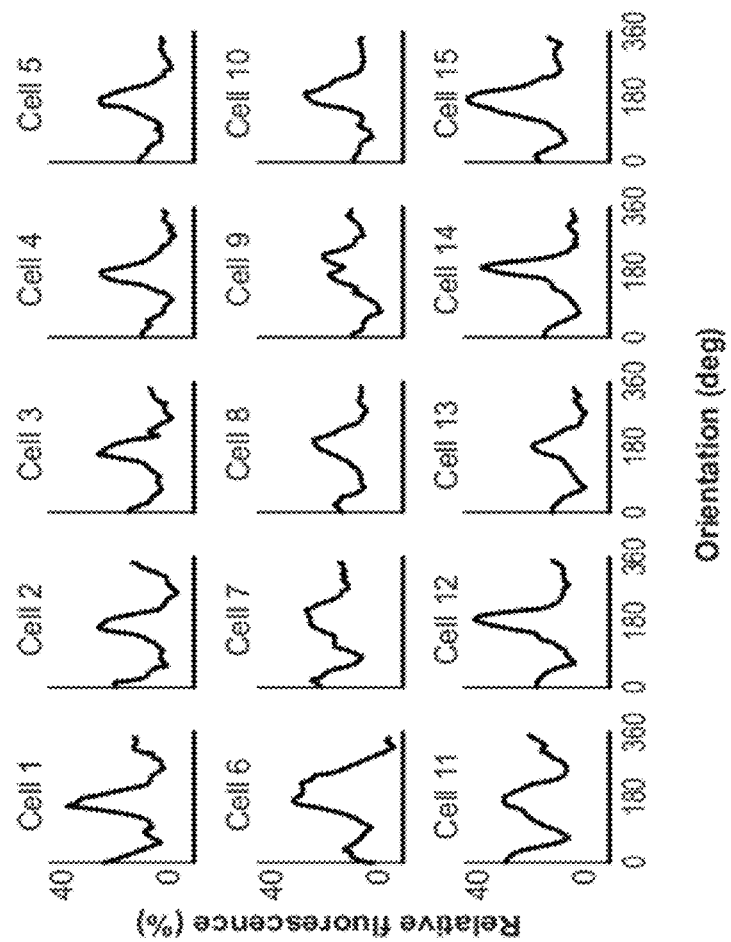
FIG. 1Ca-1Cb show two-photon fluorescence images of a cell population.
Figure 1C:
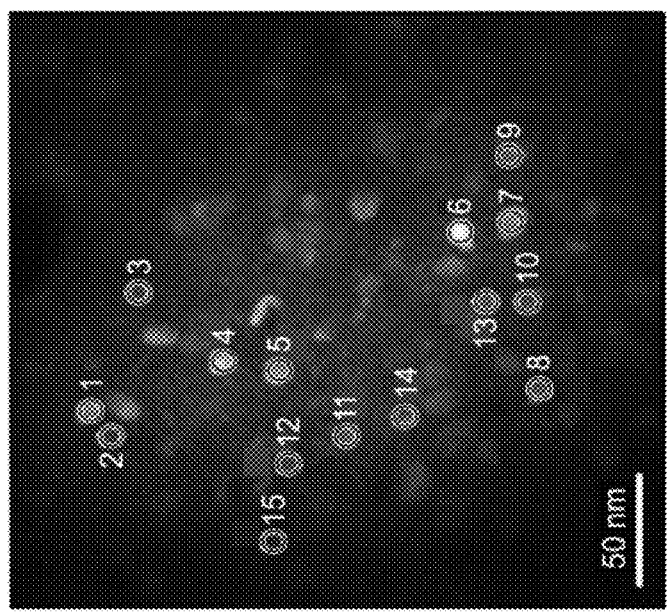

Two-photon imaging of the fluorescent calcium indicator Oregon Green Bapta (OGB) was performed in the visual cortex of anesthetized ferrets. Neurons were bulk-loaded with OGB by intracortical injection of the AM-ester conjugated form of OGB using standard techniques. Time series traces of two-dimensional images (XYT) with a field-of-view of approximately 250×250 μm were collected at 1 Hz. The images were taken from cortical layers 2/3. The stimulation method used square-wave gratings with 100% contrast which drifted at 3 Hz orthogonally to the orientation and rotated by 10° every second (each data frame). That is, the stimulus rotated 360° in 36 sec. The time series of the response of a neuron to this stimulus approximated a full orientation tuning curve. This stimulus was repeated three times in this particular embodiment. Prior to recording the stimulus responses, 10 image frames were acquired in the absence of any visual stimulus and their pixel-wise temporal means provided the estimate of the baseline level, $f_0$. Manually determined boundaries delineate the set of pixels that define each cell, and each of the 15 cells thus identified consists of 79±25 pixels (FIG. 1Ba). The data includes the time series of fluorescence on each pixel of each cell. The relative fluorescence on a given pixel is $\Delta f_k/f=(f_k-f_0)/f_0$, where $f_k$ is the $k^{th}$ time-sample of the measured fluorescence intensity, k=1, ..., K. The number of samples is K=108 in the image time-series, as each application of the periodic stimulus lasts for a selected period, in one example, 36 sec, and was repeated three times. Using the above orientation stimulus, initial anatomical images of the neuronal population can be obtained by plotting the pixel-wise maximum fluorescence across the time-series, $\max_k\{\Delta f_k\}$ (FIG. 1Ba). The relative fluorescence traces from the imaged cells (FIG. 1Bb and FIG. 1Cb) show the diversity of orientation responses in these data.

The measured fluorescence in an imaging measurement is a function of a stimulus, g(t), and noise in the system, v(t). The response, s(t) of the biological system depends on a nonlinear transformation of the stimulus input to the biological system. The effect of the input stimulus and noise on the measured fluorescence at a pixel as $$f(t)=H(s(g(t)),v(t)). \quad (1)$$

Expanding the right side of Eq. 1 in a Volterra series yields $$f(t) = \int_0^t s(g(t))K_g(t-u)du + \int_0^t v(t-u)K_v(u)du + \int_0^t\int_0^t s(g(t))K_{gg}(t-u,t-w)dudw + \int_0^t\int_0^t v(t-u)v(t-w)K_{vv}(u,w)dudw + \int_0^t\int_0^t s(g(t))v(t)K_{gv}(t-u,t-w)dudw + \ldots \quad (2)$$

Take a discrete approximation to the first two terms on the right of the above expression and assume that the second-order terms are sufficiently small so that they can be approximated as $\epsilon_k$, independent Gaussian noise with mean zero and variance $\sigma^2$. We then have $$f_k \sum_{i=1}^{L} s(g_k)K_{g,k-l} + \sum_{j=1}^{p} v_{k-j}\alpha_j + \epsilon_k \quad (3)$$

Taking the first h terms of the Fourier series expansion of g(s), $$f_k = \sum_{i=1}^{L}\left[\mu + \sum_{i=1}^{h}a_i\cos\left(\frac{2\pi i}{\tau}k\right)+b_i\sin\left(\frac{2\pi i}{\tau}k\right)\right]K_{g,k-l} + \sum_{j=1}^{p}\alpha_j v_{k-j} + \epsilon_k \quad (4)$$

where τ is the period of the input stimulus. In the two-photon imaging measurement. Assuming that the effect of the stimulus on the system is instantaneous, the discrete kernel can be written in terms of a delta function as $$K_{x,y} = \delta_{x,y} = \begin{cases} 1 & \text{if } x=y \\ 0 & \text{otherwise} \end{cases} \quad (5)$$

Substituting Eq. 5 into Eq. 4 yields $$f_k = \mu + \sum_{i=1}^{h}\left\{a_i\cos\left(\frac{2\pi i}{\tau}k\right)+b_i\sin\left(\frac{2\pi i}{\tau}k\right)\right\} + \sum_{j=1}^{p}\alpha_j v_{k-j} + \epsilon_k \quad (6)$$

which represents the effect of the stimulus on the measured signal and the noise in the image data.

Eqs. 1 and 2 are general so that many statistical models for imaging can be easily derived from them. For example, the model for fMRI data analysis takes the form $$f(t) = \int_0^t s(t)K_s(t-u)du + \int_0^t v(t-u)K_v(u)du + \epsilon(t) \\ \approx \int_0^t s(t)K_s(t-u)du + \sum_{j=1}^{q}\alpha_j v_{i-j} + \epsilon(t) \quad (7)$$

where $$K_s(t) = t^\alpha e^{\beta t}$$

is a gamma function used to model the hemodynamic response of the body, and the last term on the right is physiologic noise.

Note that equation (6) can be represented as $$f_k = s_k + v_k \tag{8}$$

where, for each k=1, ..., K, the signal is defined as the order h harmonic regression $$s_k = \mu + \sum_{i=1}^{h} \left\{ a_i \cos\left(\frac{2\pi i k}{\tau}\right) + b_i \sin\left(\frac{2\pi i k}{\tau}\right) \right\} \tag{9}$$

where $\tau$ is the period of the stimulus. Assuming that the correlated noise obeys the $p^{th}$ order autoregressive model (AR(p)) given by $$v_k = \sum_{j=1}^{p} \alpha_j v_{k-j} + \varepsilon_k \tag{10}$$

where the $\epsilon_k$ are assumed to be independent, identically distributed Gaussian random variables with zero mean and unknown variance $\sigma^2$. Assume that the zeros of the characteristic polynomial, $$1 - \sum_{j=1}^{p} a_j z^{-j},$$

are outside the unit circle to insure stationarity of the AR(p) representation. The signal is modelled as a harmonic regression because the measured fluorescence shows a strong sinusoidal response at the period of the stimulus. This smooth, periodic structure can be well described by the low-order terms of a Fourier series expansion defined by the harmonic regression model. The AR(p) model represents the highly structured physiological noise components of the fluorescence measurements.

To use the signal plus colored noise (SCN) model in Eqs. 1-3 to reduce noise in calcium imaging data, estimate its parameters $\beta=(\mu,a_1,b_1,\ldots,a_h,b_h)$, $\alpha=(\alpha_1,\ldots,\alpha_p)$ and $\sigma^2$ by maximum likelihood using a cyclic descent algorithm. The cyclic descent algorithm provides an efficient approach for solving this nonlinear estimation problem by iterating between computing the solutions to two highly tractable linear estimation problems. That is, at iteration l, given $\hat{W}^{-1(l-1)}$ the estimate of the inverse of the covariance matrix of $v_k$ from iteration l-1, the algorithm computes $\hat{\beta}^{(l)}$, the weighted least-squares estimate of $\beta$. The cyclic descent algorithm for joint estimation of harmonic and autoregressive coefficient vectors, $\hat{\beta}$ and $\hat{\alpha}$, from data vector f, is as follows.

1) Initialize $W^{(0)}=I$.
2) Let l=1.
3) $\hat{\beta}^{(l)}=(X^T W^{-1(l-1)} X^{-1} X^T W^{-1(l-1)} f$.
4) $\hat{v}^{(l)}=f-X\hat{\beta}(l)$.
5) Compute $\hat{\alpha}^{(l)}$ and $\hat{\sigma}^{2(l)}$ from $\hat{v}^{(l)}$ by Burg algorithm.
6) If $|\hat{\sigma}^{2(l)}-\hat{\sigma}^{2(l-1)}|/\hat{\sigma}^{2(l-1)}<\eta$, exit and return estimates $\{\hat{\beta}^{(l)}, \hat{\alpha}^{(l)}, \hat{\sigma}^{2(l)}\}$.
7) Compute $W^{-1(l)}$ from its Cholesky factors using Levinson-Durbin recursion.
8) Increment l and go to step 3.

Given $\hat{\beta}^{(l)}$, the algorithm computes $\hat{\alpha}^{(l)}$ and $\hat{\sigma}^{2(l)}$ using the Burg algorithm and $\hat{W}^{-1(l)}$ using the Levinson-Durbin recursion. The Burg algorithm for autoregressive (AR) coefficient estimation uses least squares forward-backward prediction error minimization and is constrained to satisfy Levinson-Durbin recursions (LDR)[34,35]. For the AR(p)model, $$v_k = \sum_{j=1}^{p} a_j v_{k-j} + \varepsilon_k,$$

the Burg algorithm estimates the coefficients $\{\alpha_1, \ldots, \alpha_p\}$ and innovations variance $\sigma^2$ given the time series $v_k$, where k=1, ..., K, as follows:

1) Let $e_k^{(0)}=v_k$ for k=2, ..., K, and $\mu_k^{(0)}=v_k$ for k=1, ..., K-1.
2) Compute $$\hat{\sigma}^{2(0)} = \frac{1}{K}\sum_{k=1}^{K} |v_k|^2.$$

3) Let l=1.

4) $\hat{\alpha}_1^{(l)} = 2 \dfrac{\sum_{k=l+1}^{K} (e_k^{(l-1)} u_{k-1}^{(l-1)})}{\sum_{k=l+1}^{K} \left(|e_k^{(l-1)}|^2 + |u_{k-1}^{(l-1)}|^2\right)}.$ 5) $\hat{\sigma}^{2(l)}=(1-|\hat{\alpha}_l^{(l)}|^2)\hat{\sigma}^{2(l-1)}$.
6) If t>1, $\hat{\alpha}_j^{(l)}=\hat{\alpha}_j^{(l-1)}-\hat{\alpha}_l^{(l)}\hat{\alpha}_{m-1}^{(m-1)}$ for j=1, ..., l-1.
7) $e_k^{(l)}=e_k^{(l-1)}-\hat{\alpha}_l^{(l)}e_{k-1}^{(l-1)}$ for k=l+1, ..., K.
8) $\mu_k^{(l)}=\mu_{k-1}^{(l-1)}-\hat{\alpha}_l^{(l)}\mu_k^{(l-1)}$ for k=t, ..., K-1.
9) If l=p, exit and return estimated AR model parameters $\{\hat{\alpha}_1^{(l)}, \ldots, \hat{\alpha}_p^{(l)}, \hat{\sigma}^{2(l)}\}$.
10) Increment l and go to Step 4.

For certain application the Cholesky factorization is used. The (K+1)×(K+1) covariance matrix of the AR process $v_k$ can be written in its Cholesky form as $W=LDL^T$. The inverse matrix $W^{-1}=L^{-T}D^{-1}L^{-1}$ is used in the cyclic descent algorithm and can be calculated efficiently using Levinson-Durbin recursions, where $$D^{-1} = \text{diag}\left(\frac{1}{\hat{\sigma}^{2(0)}}, \ldots, \frac{1}{\hat{\sigma}^{2(p)}}, \ldots, \frac{1}{\hat{\sigma}^{2(p)}}\right)$$

and $$L^{-1} = \begin{bmatrix} 1 & & & & & & \\ -\hat{\alpha}_1^{(1)} & 1 & & & & & \\ -\hat{\alpha}_2^{(2)} & -\hat{\alpha}_1^{(2)} & 1 & & & & \\ \vdots & \vdots & \vdots & & & & \\ -\hat{\alpha}_p^{(p)} & -\hat{\alpha}_{p-1}^{(p)} & -\hat{\alpha}_{p-2}^{(p)} & \cdots & & & \\ & -\hat{\alpha}_p^{(p)} & -\hat{\alpha}_{p-1}^{(p)} & \cdots & & & \\ \vdots & \vdots & \vdots & \ddots & & & \\ & & & \cdots & -\hat{\alpha}_1^{(p)} & 1 & \\ & & & \cdots & -\hat{\alpha}_2^{(p)} & -\hat{\alpha}_1^{(p)} & 1 \end{bmatrix}.$$

The coefficient and variance estimates of AR models up to order p are computed by the Burg algorithm during AR(p) model parameter estimation and are therefore already available to populate $D^{-1}$ and $L^{-1}$. Hence this is a highly efficient procedure for computing $W^{-1}$ that obviates explicit matrix inversion.

Figure 2A:
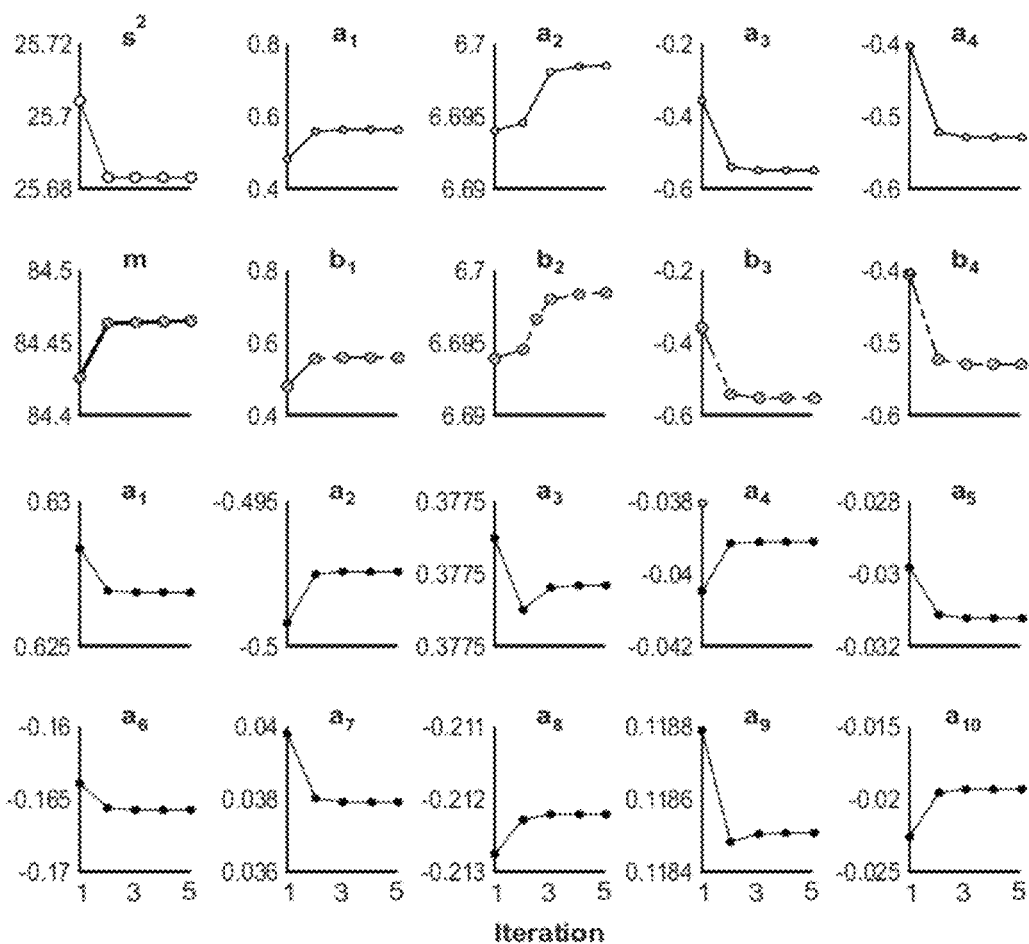
FIGS. 2Aa-2Ab show the convergence of the parameter estimates obtained with cyclic descent.
Figure 2A:
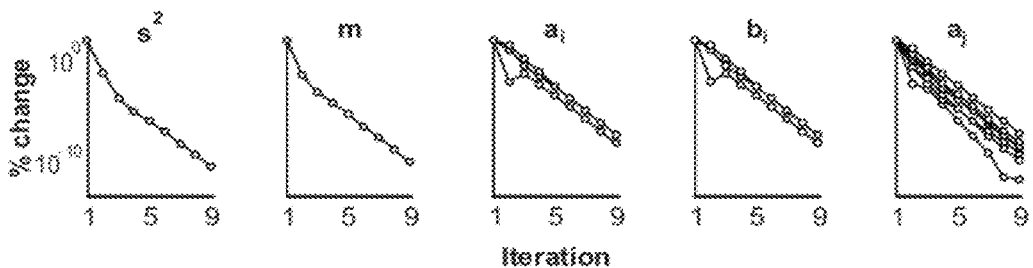

The Levinson-Durbin algorithm provides an efficient method of computing $\hat{W}^{-1(l)}$ from $\hat{\alpha}^{(l)}$ and $\hat{\sigma}^{2(l)}$. This efficiency is significant for large K since W is a K×K matrix. The stopping criterion uses the condition that the relative change in the estimate of $\hat{\sigma}^2$ between iterations is smaller than the threshold $|\hat{\sigma}^{2(l)} - \hat{\sigma}^{2(l-1)}|/\hat{\sigma}^{2(l-1)} < \eta$. If this stopping criterion is satisfied, the algorithm stops. Otherwise, given $\hat{W}^{-1(l)}$, the algorithm proceeds to iteration l+1. With this stopping criterion based on the residual variance, the cyclic descent algorithm applied to the calcium imaging data consistently converges in 3 to 5 iterations. This class of iterative algorithms are known to converge at least linearly, and these results show that the cyclic descent algorithm achieves exponential convergence (FIG. 2A). This cyclic descent algorithm avoids computing the gradients and Hessians required for Newton's procedure and the multiple iterations characteristic of the expectation maximization algorithm. A theorem due to Corradi indicates that the cyclic descent algorithm finds the global maximum of the likelihood.

Separation of the fluorescence data into signal and correlated noise relies on choosing appropriate values of h and p. To make these selections, use model selection and goodness-of-fit criteria. For preferred embodiments, these are, respectively, the corrected Akaike information criterion (AICc) and analyses of the correlation structure and spectra of the residuals from the model fits.

For the order h harmonic regression and AR(p) model, the Akaike information criterion (AIC) is defined as $$AIC = K \log \sigma^2 + 2(2h + p + 1)$$

and the corrected AIC (AICc) is given by $$AICc = AIC + \frac{2(2h + p + 1)(2h + p + 2)}{K - (2h + p + 1) - 1}$$

These criteria help determine the optimal tradeoff between model parsimony and estimation accuracy. In this SCN model, the pseudo-periodic AR component alone is capable of capturing some of the structure in the time series, reflecting the competing nature of the two model components. As an example from a representative cell, consider the AICc surface for various harmonic and AR model orders, averaged across the cell's pixels (FIG. 2Ba). When the harmonic component is absent (h=0), the AR model can capture much of the periodicity in the data, including that due to the stimulus response. The minimum of the two-dimensional AICc surface for this cell occurs at h=2 and p=2. Unlike the SCN model, the AR model alone does not decompose the data into stimulus-driven and background components. Therefore this approach fits the SCN model first with only the harmonic component (i.e. p=0 and $\hat{I}_k = \hat{s}_k + \hat{\epsilon}_k$) and uses AICc to determine the optimal harmonic order, h. In so doing, the 4 harmonics yield the minimum AICc for this cell (FIG. 2Bb). Then, fit the complete model ($\hat{I}_k = \hat{s}_k + \hat{v}_k$) to the data using the chosen h and determine the optimal AR order, p. When h=4, the optimal AR order for this cell according to AICc is 3 (FIG. 2Bb). The goodness-of-fit analysis is another important consideration whose purpose is to insure that the residuals, $\hat{\epsilon}_k$, are white to confirm that all of the systematic variance in the data has been explained by the model's harmonic and AR components. To determine the whiteness metric, the Ljung-Box portmanteau test can be used with 95% confidence applied to the first 20 lags of the residual autocorrelation function.

The AR residuals, $\epsilon_k$, have the normalized autocorrelation function (ACF) at lag $\tau$ given by $r_\tau(\epsilon) = d_\tau/d_0$, where $$d_\tau = \frac{1}{K} \sum_{m=1}^{K-\tau} (\epsilon_m - \bar{\epsilon})(\epsilon_{m+\tau} - \bar{\epsilon}).$$

The approximate 95% bounds of whiteness for the residual ACF are given by $\pm 1/\sqrt{K}$. The corresponding Ljung-Box portmanteau test statistic is $$Q = K(K+2) \sum_{\tau=1}^{T} \frac{r_\tau^2(\epsilon)}{(K-\tau)}$$

where conventionally T=20 ACF taps are considered. The null hypothesis for the whiteness test is $H_0 = Q \sim X_{\alpha, T-p}^2$, where $\alpha$ denotes the alpha level, usually taken as 5% in the analysis.

Figure 3A:
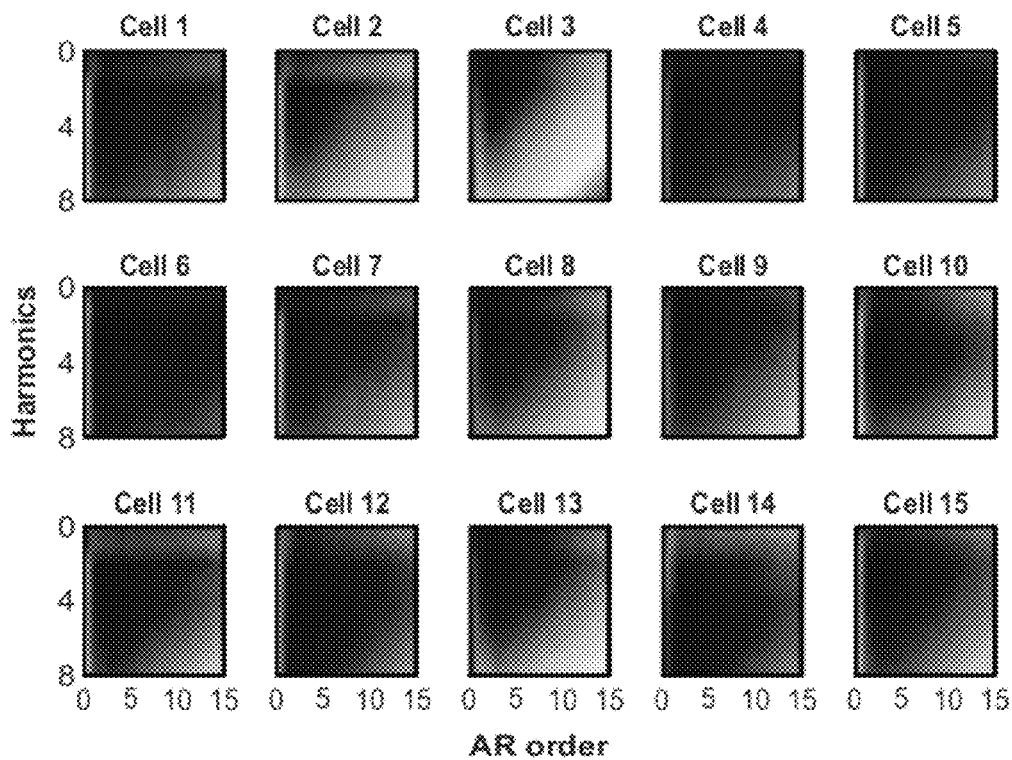
FIGS. 3Aa-3Ad show model order selection.
Figure 3A:
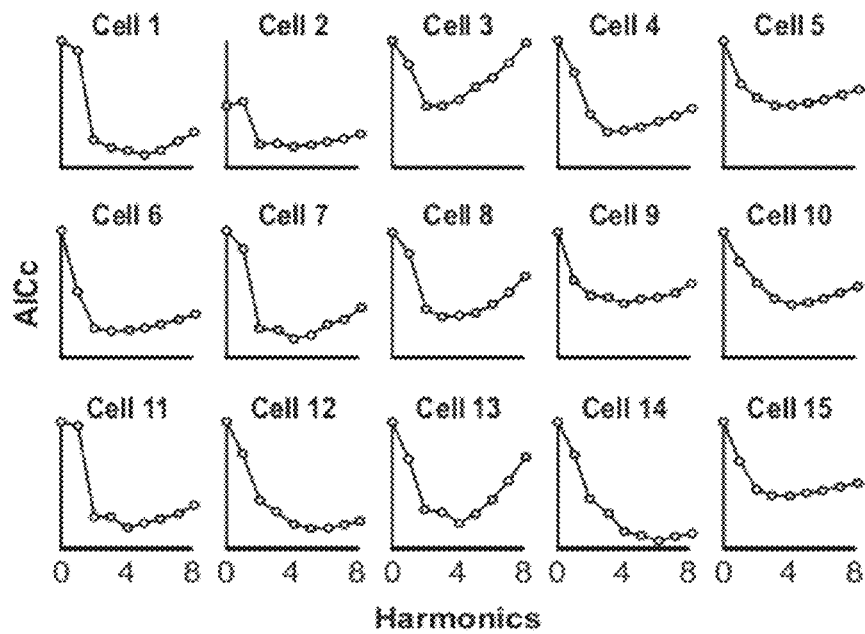
Figure 3A:
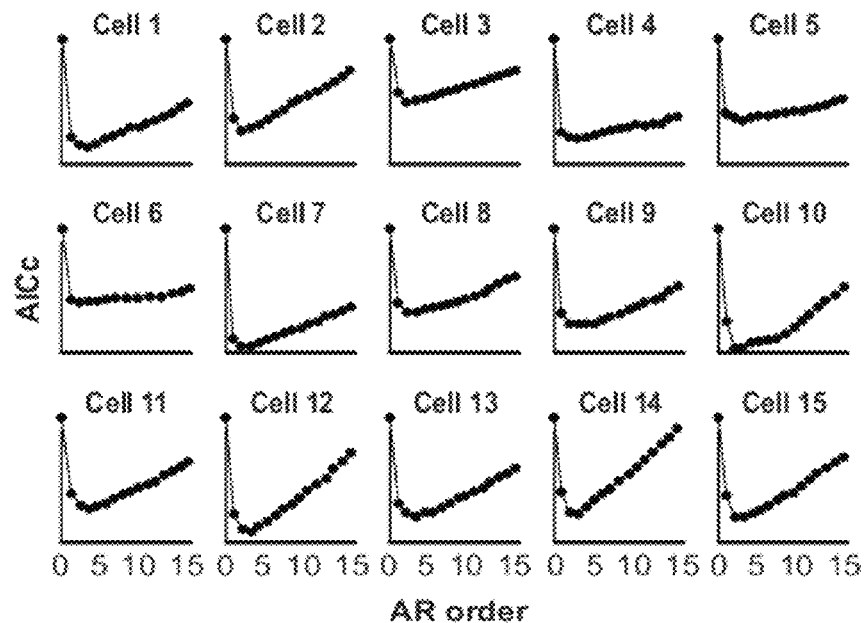
Figure 3A:
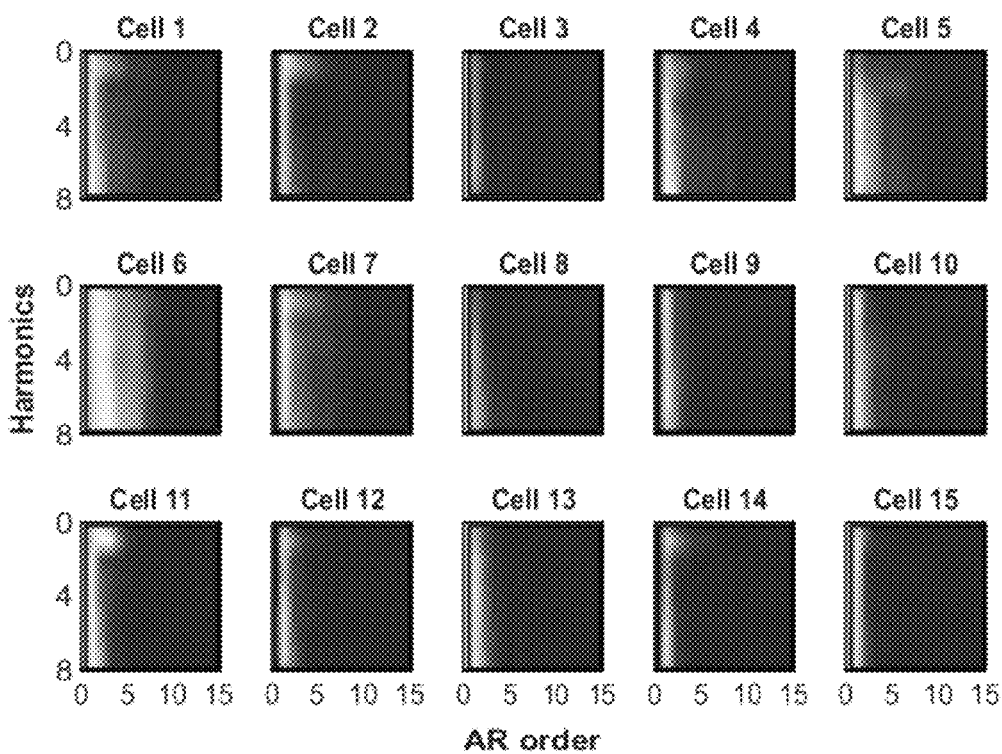

Applying this metric makes it evident that inclusion of an AR component (i.e. p>0) is necessary to obtain white residuals even when h is considerably large (FIG. 2Bc). Examination of the results obtained with inclusion of the AR component, it is apparent that the AR(3) model determined by AICc is insufficient. Instead, an AR(10) model is required to generate white residuals for this cell's data. Modelling the data with 4 harmonics and AR(10), and analyzing the spectra of the model components obtained using the fast Fourier transform, certain dominant periodicities are observed in the fluorescence data, some of which closely correspond to the stimulus frequency and its low harmonics (FIG. 2d). The harmonic component in this model, $\hat{s}_k$, captures those dominant modes in the form of a line spectrum. The nonuniform spectrum of background activity, including the significant activity observed at low frequencies, is captured by the AR component, $\hat{v}_k$. The spectrum of the residuals, $\hat{\epsilon}_k$, is approximately white. The normalized cumulative periodogram (NCP) of $\hat{v}_k$, averaged across the pixels, falls well outside the 95% whiteness bounds (FIG. 2Be). In contrast the $\hat{\epsilon}_k$ NCP nearly coincides with white noise NCP as desired. This analysis can be used to determine the required harmonic and AR model orders, which may vary from cell to cell. Note that h=4 and p=10 satisfy the above requirements for most of the cells in this data-set (FIG. 3A and Table 1).

TABLE 1

| Cell index | Optimal harmonic order from AICc | Optimal AR order from AICc | Optimal AR order from LB criterion |
|---|---|---|---|
| 1 | 5 | 3 | 10 |
| 2 | 4 | 2 | 9 |
| 3 | 2 | 2 | 7 |
| 4 | 3 | 3 | 9 |
| 5 | 3 | 3 | 11 |
| 6 | 3 | 2 | 11 |
| 7 | 4 | 3 | 9 |
| 8 | 3 | 3 | 6 |
| 9 | 4 | 3 | 10 |
| 10 | 4 | 3 | 8 |
| 11 | 4 | 3 | 8 |

TABLE 1-continued

| Cell index | Optimal harmonic order from AICc | Optimal AR order from AICc | Optimal AR order from LB criterion |
|---|---|---|---|
| 12 | 6 | 3 | 6 |
| 13 | 4 | 3 | 7 |
| 14 | 6 | 3 | 8 |
| 15 | 4 | 3 | 4 |

Table 1. Optimal harmonic and AR orders predicted by AICc and Ljung-Box test for each cell. Based on these results, for this data set, a good fit to the data is obtained with 4 harmonics and about 10 AR coefficients.

Therefore these values are used for further analysis. Once the optimal order for the SCN model has been determined and the goodness-of-fit assessment completed, the model is used to make biological determinations.

Figure 3B:
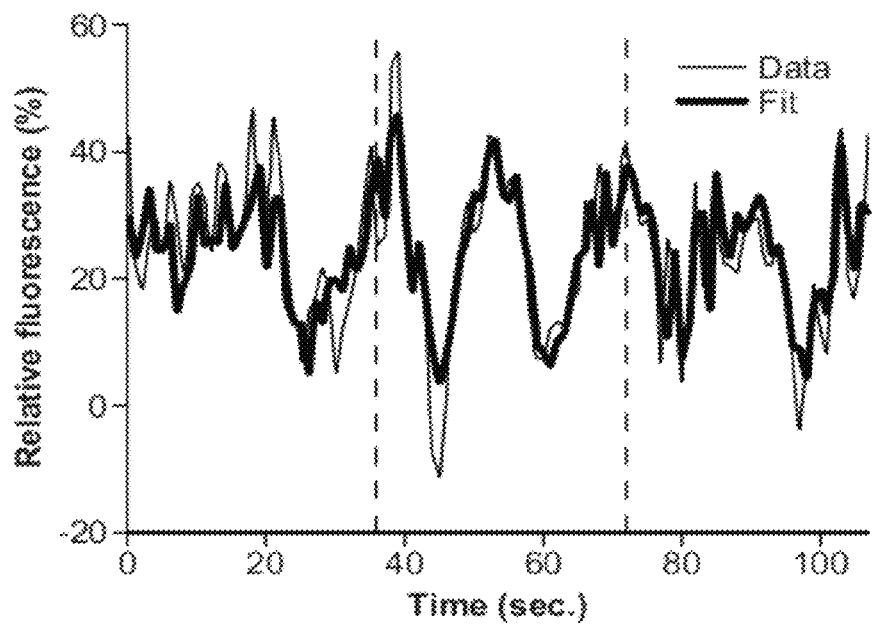
FIGS. 3Ba-3Be show decomposition of fluorescence time traces into signal and noise components for Cell 11, Pixel 45.
Figure 3B:
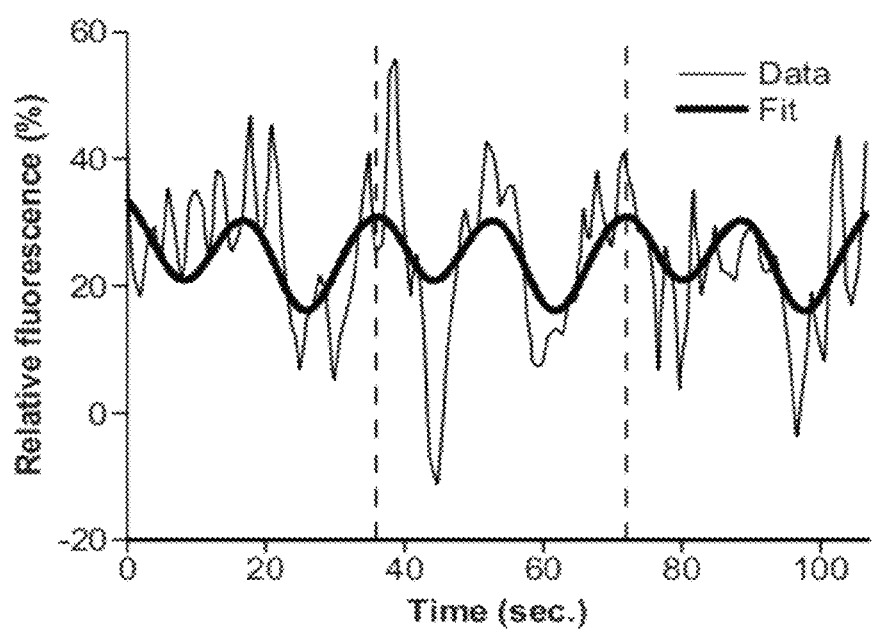
Figure 3B:
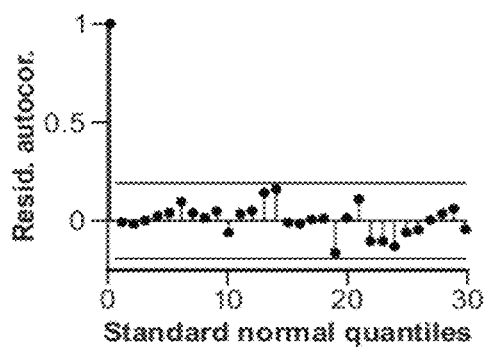
Figure 3B:
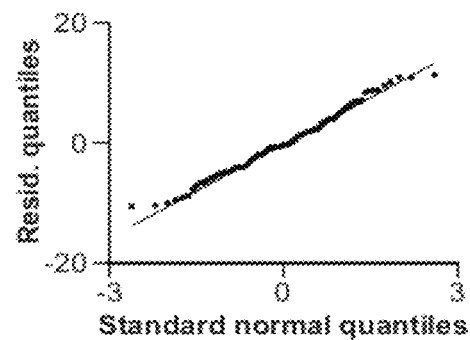
Figure 3B:
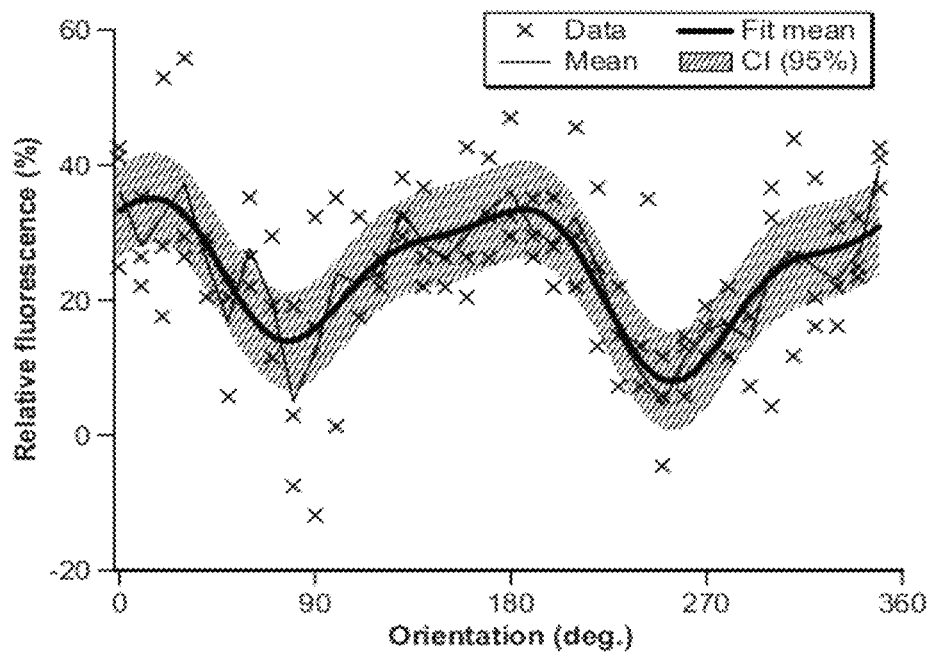

The SCN model can be used to characterize the relative fluorescence response to the stimulus at a single pixel. The close fit between the data and the signal estimate establishes the validity of this model (FIG. 3Ba). The signal component, $\hat{s}_k$, provides a denoised estimate of the response for three trials of stimulus presentation (FIG. 3Bb). The autocorrelation function and quantiles of the residual, $\hat{\epsilon}_k$, confirm that it is consistent with an independent Gaussian process (FIG. 3Bc and Bd). Then, construct the denoised response tuning curve, $\hat{u}(\phi)$, where $\phi$ is the orientation, along with the approximate 95% confidence intervals and analyze the response characteristics.

For the $i^{th}$ harmonic regression coefficient, $\beta_i$, estimated by the weighted least squares procedure, the approximate 95% confidence intervals are given by $$\hat{\beta}_i - se_i t\alpha/2, K-2h-1 \leq \beta_i \leq \hat{\beta}_i + se_i t\alpha/2, K-2k-1$$

where $\hat{\beta}_i$ is the coefficient estimate, $\alpha=0.05$ and $se_i = \sqrt{(X^{T\hat{W}^{-1}}X)_{ii}^{-1}}$. Similarly, for the $j^{th}$ AR coefficient, $\psi_j$, the confidence intervals $$\hat{\psi} - se_j t\alpha/2, K-p \leq \psi_j \leq \hat{\psi}_j + se_j t\alpha/2, K-p$$

where $se_j = \sqrt{\frac{\sigma^2}{K-p}(\hat{V}^T\hat{V})_{jj}^{-1}}$ and $$\hat{V} = \begin{bmatrix} \hat{v}_{-1} & \cdots & \hat{v}_{-j} \\ \vdots & \ddots & \vdots \\ \hat{v}_{K-1} & \cdots & \hat{v}_{K-j} \end{bmatrix}$$

is a K×p matrix containing the time-lagged samples of the AR process. Based on these, use a t-test of significance for the coefficients. The alternate hypothesis for the harmonic model is $$H_1: \left|\frac{\hat{\beta}_i}{se_i}\right| > t\alpha/2, K-2h-1$$

and similarly, for the AR model:

$$H_1: \left|\frac{\hat{\psi}_i}{se_i}\right| > t\alpha/2, K-p.$$

The corresponding parameter is significant if the hypothesis is rejected.

This signal estimate (FIG. 3Be) captures the key features of the neuronal response, such as the location and width of tuning to the stimulus effect. The use of a Gaussian or cosine curve to fit the data can constrain the response estimate to have a simple, symmetric shape. The present model allows the tuning curve estimate to reflect faithfully the complex shape of the cell response observed in the data with minimal computational complexity.

Denoised images can be constructed using the signal component estimate, $\hat{s}_k$, at each pixel. A comparison of the fluorescence response estimates of pixels around a cell obtained with conventional across-trial averaging and with the SCN model (FIG. 4a) demonstrates the enhanced image contrast and clarity provided by the model. This denoising method delineates the stimulus response within the cell soma and allows improved observation of calcium dynamics around the cell associated with excitation. In a second cell (FIG. 4b), the background activity at the bottom of the frame is substantially reduced in intensity by this method. The increased contrast of the denoised images reveals additional subcellular processes not discernible in the conventional images obtained by averaging (FIG. 4c). This enables characterization of the source of these signals and their behaviour.

By denoising two-photon imaging data with the SCN model, reliable estimates of several quantities are provided that can be used to describe neuronal behaviour. For example, the orientation preferences of the primary visual cortex neurons in the sample can be measured. At each pixel, the preferred orientation, $\bar{\phi}$, is obtained as the orientation at which the denoised tuning curve peak occurs, i.e., $\bar{\phi}=$ arg max$_\phi\{\hat{\mu}(\phi)\}$. Note that the neighbouring cells show a preference for similar orientations with a smooth spatial variation (FIGS. 5a and c). Among the cells, there are different degrees of deviation from the mean preferred orientation (FIG. 5d). This deviation is particularly high for two of the cells possibly due to somatic and dendritic dynamics. Calculate the orientation selectivity from the tuning curve $\hat{\mu}(\phi)$ as the half-width at half-height. Analysis of orientation selectivity at each pixel reveals both spatial trends and intra-cellular variations (FIG. 5b). A wide-ranging level of orientation selectivity is apparent (FIG. 5e). These examples demonstrate that the SCN model can facilitate a variety of functional analyses with high reliability.

For a circular random variable, $\phi$, the circular mean is calculated as $$\bar{\varphi} = \tan^{-1} \frac{\sum_{i=1}^{n} \sin\varphi_i}{\sum_{i=1}^{n} \cos\varphi_i}$$

with its 95% confidence interval given by $$\bar{\phi} \pm \sin^{-1}(z\alpha/2\sigma_\phi)$$

Take, for example, $\alpha=0.05$, $\sigma_\phi=\sqrt{\delta_\phi/N}$ is the circular standard error, and $\delta_\phi=[1-N^{-1}\sum_{i=1}^{N}\cos 2(\phi_i-\bar{\phi})]/2N^{-1}\sum_{i=1}^{N}\cos(\phi_i-\bar{\phi})$ is the circular dispersion.

The ratio of stimulus-evoked response (signal) to background activity (colored noise) provides a natural definition of the neuronal signal-to-noise ratio (SNR) and a way to compare the relative responsiveness of the cells to the stimulus. Calculate the signal power from the harmonic model as $$P_2 = \frac{1}{2}\sum_{i=1}^{n} |a_i|^2 + |b_2|^2. \quad (11)$$

The total power of the autoregressive model is $$P_v = \int \sigma^2 \left|1 - \sum_{j=1}^{p} \alpha_j e^{-2\pi i j f}\right|^{-2} df. \quad (12)$$

It follows that the SNR can be computed as the ratio of the signal power to the colored noise power as $$SNR = \frac{P_s}{P_v}. \quad (13)$$

Figure 6A:
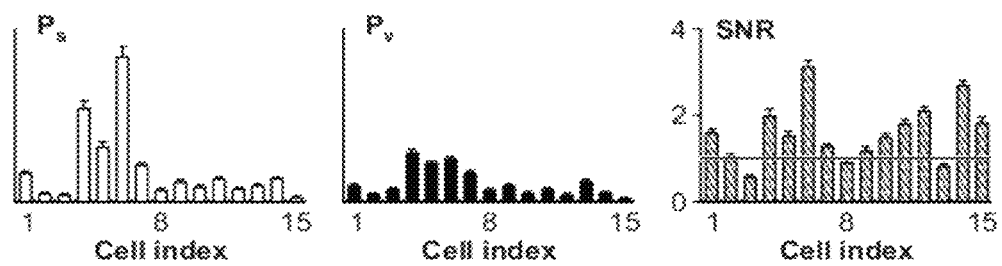
FIGS. 6A-6B show the neuronal signal-to-noise ratio (SNR) estimated using the SCN model; The SNR is the ratio of the power of stimulus-evoked signal to that of stimulus-free background activity.
Figure 6B:
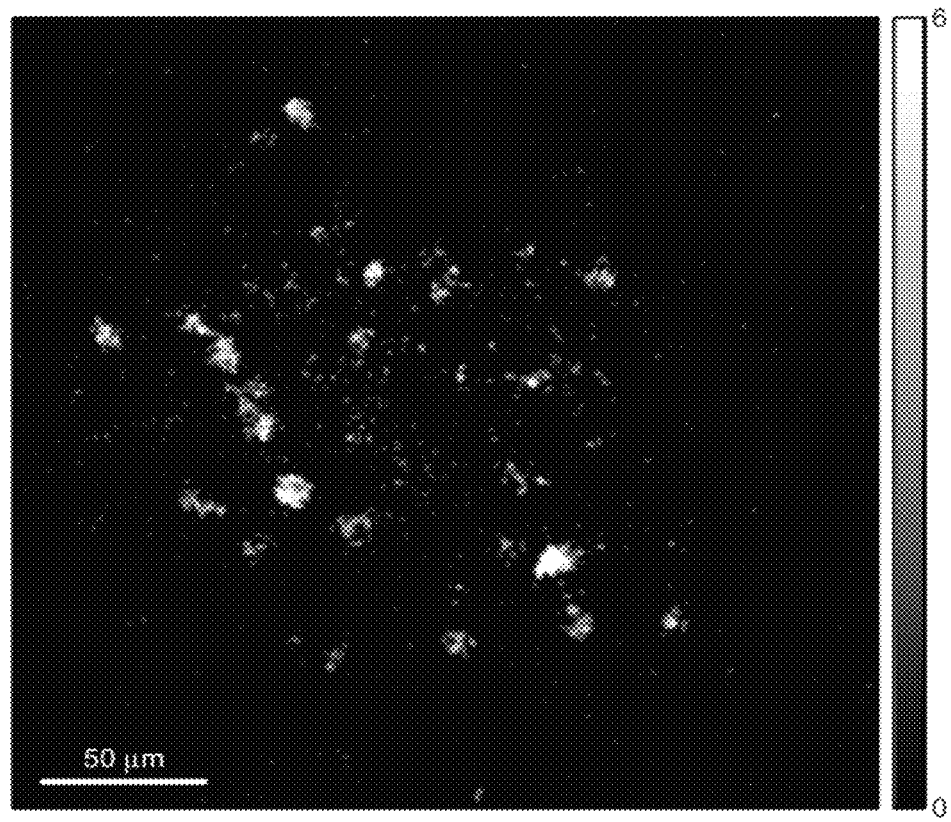

The cells in the data set exhibit a wide range of SNRs (FIG. 6a). The locations of the cells with high SNR (FIG. 6b) agree closely with the anatomical map (FIG. 1Ba), and therefore the pixel-wise SNR maps can be used to identify robustly the locations of cells that respond to the given stimulation.

Figure 7:
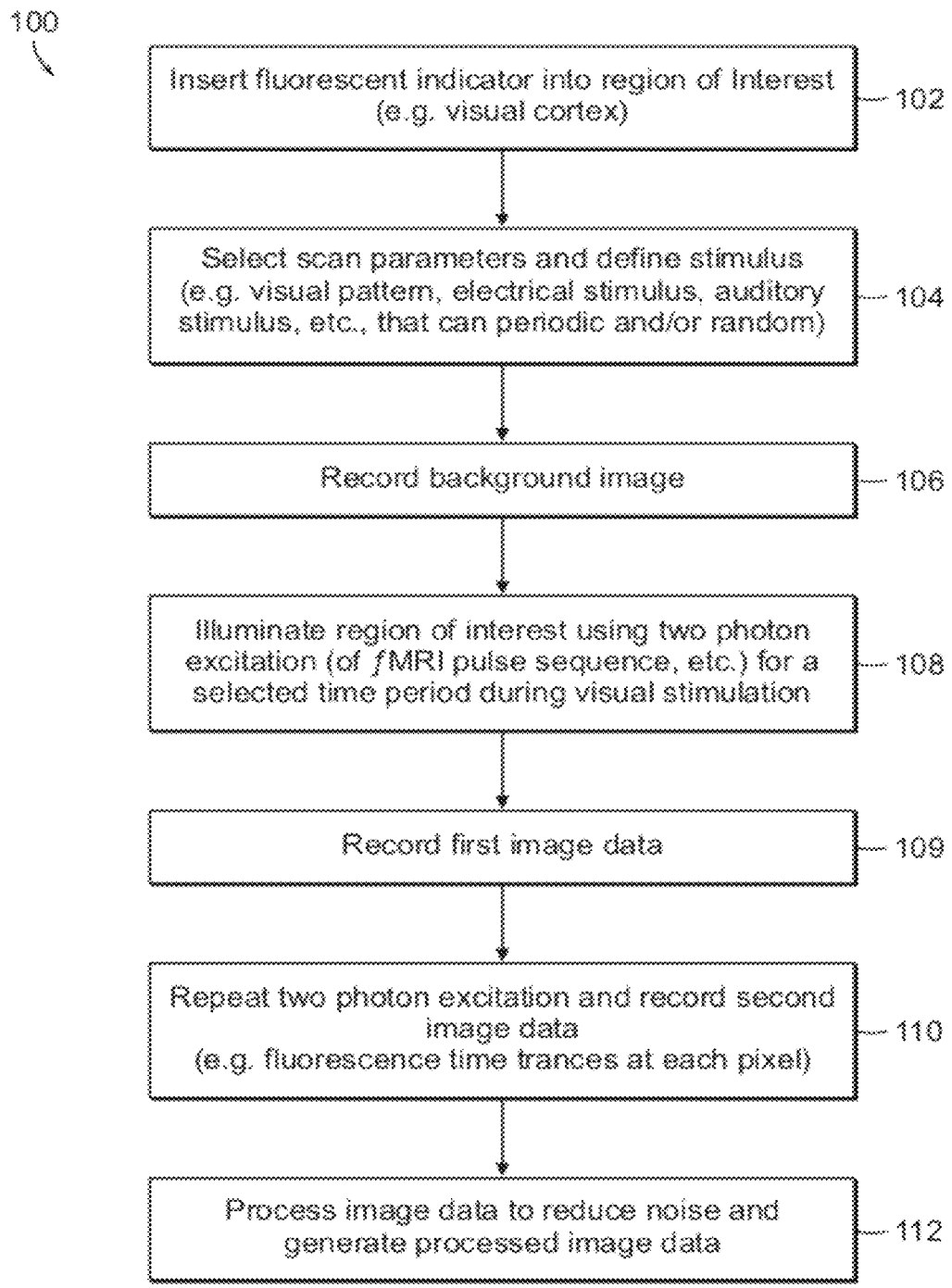
FIG. 7 illustrates a process sequence for acquisition of image data in accordance with preferred embodiments of the invention.

A process sequence illustrating a method 100 of acquiring image data in accordance with preferred embodiments of the invention is illustrated in FIG. 7. A fluorescent indicator, or other agent, is inserted 102 into the region of interest. Scan parameters are selected 104 to define an illumination pattern, or to select parameters for the data collection process, such as the pulse sequence for fMRI imaging procedure. A background image can be recorded 106. The region of interest can then be illuminated 108 using, for example, two photon excitation for a selected period of time during a stimulus period. First image data is recorded 109 and optionally processed in real time. A second illumination period 110 (or additional data collection periods) can be performed to record second image data with the same or different scan parameters. The image data is then processed 112 to reduce noise and thereby generate processed image data.

Figure 8:
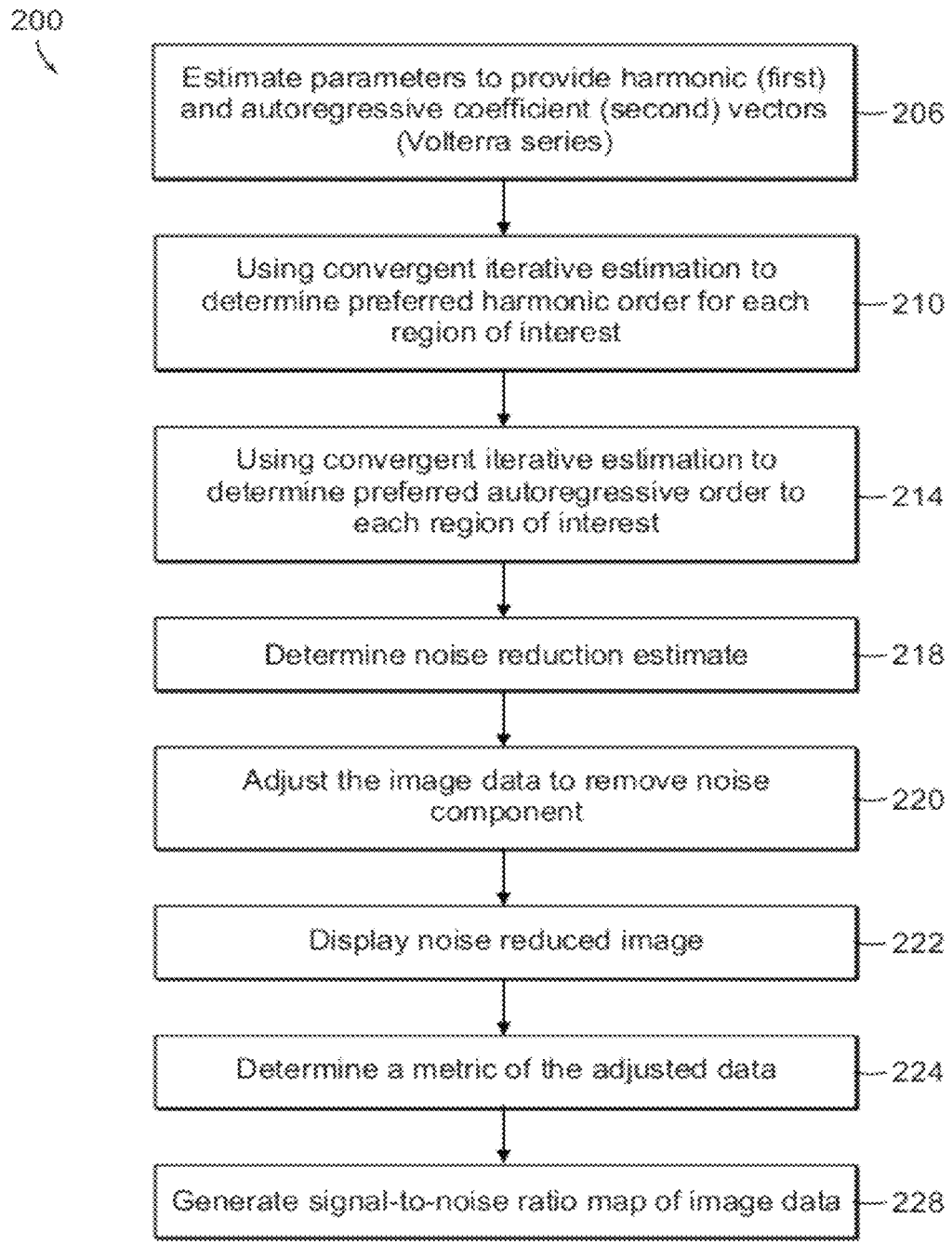
FIG. 8 illustrates a process sequence for analyzing data to reduce noise image data in accordance with preferred embodiments of the invention.

Illustrated in FIG. 8 is a process sequence 200 for the processing of image data in accordance with preferred embodiments of the invention. As described herein in greater detail, the parameters for the harmonic (first) and autoregressive (second) vectors are estimated 206. Using a converging iterative (cyclic descent) process 206. The preferred harmonic order and the preferred autoregressive order are then determined 210, 214. The processor then formulates 218 the selected parameters (filter) to be applied to the noise. The processor then applies 220 this to the data to remove the noise from the image data which can then be displayed 222. From this denoised image additional details can be generated a metric 224 characterizing the quality of the adjusted data and/or a map of the signal-to-noise ratio 228.

While this invention has been particularly shown and described with reference to preferred embodiments and equivalents thereof, it will be understood by those skilled in the art that various changes in form and details may be made therein without departing from the scope of the invention encompassed by the appended claims.

What is claimed is:

1. A computer implemented method for reducing a noise component of image data comprising:
   stimulating a sensory response in a region of interest in a biological material with a stimulus to induce a neural response;
   detecting signals associated with the neural response in a plurality of cells that are spatially distributed within the biological material to generate detected neural response image data;
   recording the detected neural response image data;
   processing the neural response image data with a data processor, the data processor being programmed to process the neural response image data with an analytic representation to separate a stimulus response component and a noise component, the stimulus response component being represented by a vector having an order determined by a convergent iterative process; and
   generating processed neural response image data to generate reduced noise neural response image data.

2. The method of claim 1 further comprising forming the analytic representation including the steps of:
   determining an harmonic vector and an autoregression vector;
   determining an harmonic order;
   determining an autoregressive order;
   separating the stimulus response component of the image data from the noise component using the harmonic order and the autoregressive order.

3. The method of claim 1 further comprising generating a map of signal-to-noise ratio of the image data.

4. The method of claim 1 wherein the representation further comprises a Volterra series.

5. The method of claim 1 wherein the representation further comprises a Fourier series.

6. The method of claim 1 wherein the image data comprises at least one of magnetic resonance imaging data, fluorescence image data, optical imaging data or computed tomography data.

7. The method of claim 1 wherein the step of recording image data further comprises illuminating the region of interest with light and recording fluorescence intensity of light from the region of interest in response to the illuminating step.

8. The method of claim 1 wherein the stimulating step further comprises using a sensory stimulus comprising at least one of an auditory stimulus, a contact stimulus, an electrical stimulus and a visual stimulus.

9. The method of claim 1 wherein the recording step further comprises illuminating tissue with two photon excitation light.

10. The method of claim 9 further comprising rotating an illumination light beam path relative to the region of interest.

11. The method of claim 1 further comprising imaging brain tissue.

12. The method of claim 1 further comprising imaging a calcium distribution in the plurality of cells that are distributed within tissue.

13. The method of claim 1 further comprising illuminating a visual cortex of a mammalian body to measure a neural response of cells within the visual cortex.

14. The method of claim 1 further comprising determining residual white noise in the recorded image data.

15. The method of claim 1 further comprising applying a visual stimulus to a visual cortex.

16. The method of claim 15 wherein the step of applying a visual stimulus comprises displaying a varying pattern on a display.

17. The method of claim 1 further comprising detecting the image data with a detector and processing the image data with a data processor.

18. The method of claim 1 wherein the representation comprises a Volterra series.

19. The method of claim 1 wherein the processing step further comprises representing a dynamic stimulus neural response.

20. The method of claim 1 further comprising displaying an image of a cellular response to the stimulus.

21. The method of claim 1 further comprising separating a harmonic component of the image data from an autoregressive component.

22. The method of claim 1 wherein the processing step further comprises a convergent iterative process.

23. The method of claim 1 further comprising separating a harmonic component of the image data from an autoregressive component.

24. The method of claim 1 further comprising displaying a cellular response to the stimulus on an electronic display.

25. A system for processing neural image data comprising:
an imaging system that generates image data to record a spatial distribution of a plurality of cells within a region of tissue;
a sensory stimulation source that generates a neural response in the plurality of cells to a sensory stimulus; and
a data processor that receives the image data of the neural response within the plurality of cells from the imaging system, the data processor being adapted for processing neural response image data with an analytic representation separating a first component represented by a vector having a first order term associated with the neural response to the sensory stimulus, the first order term having an order determined by a convergent iterative process and a noise component having a second order term, the data processor being operative to reduce the noise component in the image data and generate processed neural response image data stored in a memory.

26. The system of claim 25 wherein the stimulation source is operative to induce a dynamic response in a region of interest in a biological material.

27. The system of claim 25 further comprising a filter that filters the image data to reduce a noise component in the image data.

28. The system of claim 25 wherein the stimulation source comprises a display.

29. The system of claim 25 wherein the imaging system comprises a two-photon imaging system to record a fluorescence response of a biological system, the imaging system including an image data display.

30. The system of claim 25 wherein the noise component is represented as a second vector having an order determined by a convergent iterative process.

31. The system of claim 25 wherein the imaging system further comprises an illumination source and a detector connected to the data processor.

32. The system of claim 31 wherein the imaging system comprises a magnetic resonance imaging system.

33. The system of claim 31 wherein the imaging system comprises a tomography system.

34. The system of claim 31 wherein the imaging system comprises an optical illumination source and a light detector.

35. The system of claim 34 wherein the light detector comprises a photomultiplier tube.

36. A method of reducing noise in image data comprising:
illuminating a region of interest in tissue with light from a light source;
stimulating a neural response in a plurality of cells within the tissue with a sensory stimulus;
detecting light from the plurality of cells within the tissue in response to the illuminating light to record an image of a neural response within the tissue and generate neural response image data; and
processing the neural response image data with a data processor, the data processor being programmed to use an analytic representation to generate a stimulus response component and a noise component of the neural response image data to provide reduced noise neural response data, the stimalus response componet being representative by a vector having an order determined by a convergent iterative process.

37. The method of claim 36 further comprising illuminating the tissue with a multiphoton light source.

38. The method of claim 36 wherein the processing step further comprises reducing noise in the neural response image data.

39. The method of claim 36 further comprising imaging cells within the tissue.

40. The method of claim 36 further comprising scanning the illuminating light across a region of a visual cortex of a subject and detecting fluorescence.

41. The method of claim 36 further comprising detecting fluorescence in the tissue.

42. The method of claim 36 further comprising detecting calcium fluorescence in the tissue.

43. The method of claim 36 wherein the processing step further comprises using an analytic representation to compute a dynamic component and a noise component in a detected image of the tissue.

44. A computer implemented method for reducing a noise component of image data comprising:
stimulating a sensory response in a region of interest in a biological material with a stimulus to induce a neural response;
recording image data of the neural response to the stimulus;
processing the neural response image data with a data processor, the data processor being programmed to process the neural response imaged data with an analytic representation to separate a stimulus response component including an harmonic order and a noise component including an autoregressive order, the stimulus response component being represented by a vector having the harmonic order that is determined by a convergent iterative process; and
generating processed neural response image data to record reduced noise image data.

45. The method of claim 44 further comprising generating a map of signal-to-noise ratio of the image data.

46. The method of claim 44 wherein the analytic representation further comprises a Volterra series.

47. The method of claim 44 wherein the image data comprises at least one of magnetic resonance imaging data, fluorescence image data, optical imaging data or computed tomography data.

48. The method of claim 44 further comprising storing the reduced noise image data in a memory and displaying reduced noise image data on a display.

* * * * *